US012203944B2

United States Patent
Kampf et al.

(10) Patent No.: US 12,203,944 B2
(45) Date of Patent: Jan. 21, 2025

(54) METHODS AND COMPOSITIONS FOR EVALUATION AND TREATMENT OF RENAL INJURY AND RENAL FAILURE BASED ON C-C MOTIF CHEMOKINE LIGAND 14 MEASUREMENT

(71) Applicant: ASTUTE MEDICAL, INC., San Diego, CA (US)

(72) Inventors: James Patrick Kampf, San Diego, CA (US); Paul McPherson, Encinitas, CA (US); Donald Chalfin, Berkeley, CA (US)

(73) Assignee: Astute Medical, Inc., San Diego, CA (US)

( * ) Notice: Subject to any disclaimer, the term of this patent is extended or adjusted under 35 U.S.C. 154(b) by 340 days.

(21) Appl. No.: 17/739,009

(22) Filed: May 6, 2022

(65) Prior Publication Data
US 2023/0025225 A1    Jan. 26, 2023

Related U.S. Application Data

(63) Continuation of application No. 16/475,326, filed as application No. PCT/US2018/013561 on Jan. 12, 2018, now Pat. No. 11,353,465.

(60) Provisional application No. 62/445,692, filed on Jan. 12, 2017.

(51) Int. Cl.
    *G01N 33/68* (2006.01)
(52) U.S. Cl.
    CPC ............ *G01N 33/6893* (2013.01); *G01N 2333/521* (2013.01); *G01N 2800/347* (2013.01); *G01N 2800/56* (2013.01)
(58) Field of Classification Search
    CPC ......... G01N 33/6893; G01N 2800/347; G01N 2800/56; G01N 2333/521
    See application file for complete search history.

(56) References Cited

U.S. PATENT DOCUMENTS

| | | | |
|---|---|---|---|
| 5,480,792 A | 1/1996 | Buechler | |
| 5,525,524 A | 6/1996 | Buechler et al. | |
| 5,571,698 A | 11/1996 | Ladner et al. | |
| 5,631,171 A | 5/1997 | Sandstrom et al. | |
| 5,679,526 A | 10/1997 | Buechler et al. | |
| 5,824,799 A | 10/1998 | Buechler et al. | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,955,377 A | 9/1999 | Maul et al. | |
| 5,985,579 A | 11/1999 | Buechler et al. | |
| 6,019,944 A | 2/2000 | Buechler | |
| 6,057,098 A | 5/2000 | Buechler et al. | |
| 6,113,855 A | 9/2000 | Buechler et al. | |
| 6,143,576 A | 11/2000 | Buechler | |
| 7,833,732 B2 | 11/2010 | Hamid | |
| 9,410,968 B2 | 8/2016 | Meyer et al. | |
| 2003/0157573 A1 | 8/2003 | Mor | |
| 2004/0152169 A1 | 8/2004 | Gentz et al. | |
| 2009/0042826 A1 | 2/2009 | Mor et al. | |
| 2011/0059537 A1 | 3/2011 | Liangos et al. | |
| 2012/0283128 A1* | 11/2012 | Anderberg ......... G01N 33/6893 422/69 |
| 2018/0209990 A1 | 7/2018 | Anderberg et al. | |

FOREIGN PATENT DOCUMENTS

| | | | |
|---|---|---|---|
| CN | 1646695 | 7/2005 | |
| CN | 102187219 | 9/2011 | |
| CN | 102725636 | 10/2012 | |
| EP | 2479566 | 7/2012 | |
| EP | 2666872 | 11/2013 | |
| WO | WO 2010/048347 | 4/2010 | |
| WO | WO 2011/017682 | 2/2011 | |
| WO | WO 2011/057138 | 5/2011 | |
| WO | WO 2011/162819 | 12/2011 | |
| WO | WO 2011/162820 | 12/2011 | |
| WO | WO 2011/162821 | 12/2011 | |
| WO | WO 2012/177717 | 12/2012 | |
| WO | WO 2013/043310 | 3/2013 | |
| WO | WO 2013/086359 | 6/2013 | |
| WO | WO 2013/096740 | 6/2013 | |
| WO | WO 2016/064877 | 4/2016 | |
| WO | WO-2016064877 A2 * | 4/2016 | ......... G01N 33/6863 |
| WO | WO 2018/132702 | 7/2018 | |

OTHER PUBLICATIONS

Extended European Search Report issued Aug. 26, 2022, in European application (No. 22155208.6).
Official Action issued May 27, 2023, in Chinese Patent Application (No. 202111365747.3).
Official Action issued Aug. 3, 2023, in European application (No. 22155208.6).
Official Action issued May 23, 2023, in Japanese Patent Application (No. 2022-044473).
Bagshaw et al., "A multi-centre evaluation of the RIFLE criteria for early acute kidney injury in critically ill patients," Nephrol Dial Transplant, 2008, 23(4):1203-1210.
Bellomo et al., "Acute renal failure—definition, outcome measures, animal models, fluid therapy and information technology needs: the Second International Consensus Conference of the Acute Dialysis Quality Initiative (ADQI) Group," Crit Care, 2004, 8(4):R204-R212.
Chertow et al., "Acute Kidney Injury, Mortality, Length of Stay, and Costs in Hospitalized Patients," J Am Soc Nephrol, 2005, 16(11):3365-3370.
Chung et al., "Chemokines in Renal Injury," J Am Soc Nephrol , Dec. 31, 2011, 22:802-809.

(Continued)

*Primary Examiner* — Vanessa L. Ford
*Assistant Examiner* — Sandra Carter

(57) ABSTRACT

The present invention relates to methods and compositions for monitoring, diagnosis, prognosis, and determination of treatment regimens in subjects suffering from or suspected of having a renal injury. In particular, the invention relates to using assays that detect C-C motif chemokine 14 as diagnostic and prognostic biomarker assays in renal injuries.

21 Claims, No Drawings

Specification includes a Sequence Listing.

(56) References Cited

OTHER PUBLICATIONS

Cwirla et al., "Peptides on phage: A vast library of peptides for identifying ligands," Proc Natl Acad Sci USA, 1990, 87(16):6378-6382.
Devlin et al., "Random Peptide Libraries: A Source of Specific Protein Binding Molecules," Science, Jul. 27, 1990, 249(A967):404-406.
Fassett et al., "Biomarkers in chronic kidney disease: a review," Kidney International, Jun. 22, 2011, 80:806-821.
Fischer et al., "A readers' guide to the interpretation of diagnostic test properties: clinical example of sepsis," Intensive Care Med, 2003, 29(7):1043-1051.
Fry et al., "Management of acute renal failure," Postgrad Med J, 2006; 82:106-116.
Gunnerson et al., "TIMP2. IGFBP7 biomarker panel accurately predicts acute kidney injury in high risk surgical patients," J Trauma Acute Care Surg, Oct. 30, 2015, 80(2):243-249.
Gustafsson et al., "Gas6 and the Receptor Tyrosine Kinase Axl in Clear Cell Renal Cell Carcinoma," PLoS One, 4(10):1-10.
Hanley et al., "The meaning and use of the area under a receiver operating characteristic (ROC) curve," Radiology, Apr. 1982;143(1):29-36.
Haringman et al., "Chemokine and chemokine receptor expression in paired peripheral blood mononuclear cells and synovial tissue of patients with rheumatoid arthritis, osteoarthritis, and reactive arthritis," Ann Rheum Dis, Mar. 2006, 65(3): 294-300.
Jialin, "Refractory Urinary System Diseases," Shanghai Science and Technology Press, Dec. 31, 2007, pp. 343-346 (partial translation).
Jiang et al., "Progress in the Research of Tyro 3 Receptor Tyrosine Kinases Subfamily," Chinese Journal of Histochemistry and Cytochemistry, Aug. 31, 2005, 14(4):466-46—English Abstract only.
Kashani et al., "Discovery and validation of cell cycle arrest biomarkers in human acute kidney injury," Critical Care, 2013, 17(1):R25 (12 pp).
KDIGO Clinical Practice Guideline for Acute Kidney Injury, "Kidney International Supplements," Official Journal of the International Society of Nephrologoy, Mar. 2012, 2(1):1-138.
Kellum, "Acute kidney injury," Crit Care Med, 2008, 36(4 Suppl):S141-S145.
Lassnigg et al., "Minimal Changes of Serum Creatinine Predict Prognosis in Patients after Cardiothoracic Surgery: A Prospective Cohort Study," J Am Soc Nephrol, 2004, 15(6):1597-1605.
McCullough et al., "Contrast-Induced Nephropathy (CIN) Consensus Working Panel: Executive Summary," Rev Cardiovasc Med, 2006, 7(4):177-197.
Mehta et al., "Acute Kidney Injury Network: report of an initiative to improve outcomes in acute kidney injury," Crit Care, 2007, 11(2):R31 (8 pp).
Moreno et al., "Role of chemokines in proteinuric kidney disorders," Feb. 28, 2014, Expert Reviews in Molecular Medicine, 16:1-22—Abstract only.
Nelson et al., "A computer program for calculating antibody affinity constants," Comput Methods Programs Biomed, 1988, 27(1):65-68.
Paul, "Biomarkers of Renal Tumor Burden and Progression in TSC," Massachusetts General Hospital, Sep. 2013.
Praught et al., "Are small changes in serum creatinine an important risk factor?," Curr Opin Nephrol Hypertens, 2005, 14(3):265-270.
Ricci et al., "The RIFLE criteria and mortality in acute kidney injury: A systematic review," Kidney Int, 2008, 73:538-546.
Schulz-Knappe et al., "HCC-1, a Novel Chemokine From Human Plasma," J Exp Med, Jan. 1, 1996, 183(1):295-299.
Scott et al., "Searching for Peptide Ligands with an Epitope Library," Science, Jul. 27, 1990, 249:386-390.
Van Erp et al., "Application of a Sol Particle Immunoassay to the Determination of Affinity Constants of Monoclonal Antibodies," J Immunoassay, 1991, 12(3):425-443.
Ward et al., "Binding activities of a repertoire of single immunoglobulin variable domains secreted from *Escherichia coli*," Nature, Oct. 12, 1989, 341:544-546.
Wijeysundera et al., "Derivation and Validation of a Simplified Predictive Index for Renal Replacement Therapy After Cardiac Surgery," JAMA, Apr. 25, 2007, 297:1801-1809.
Wilson et al., "Simplified conjugation chemistry for coupling peptides to F(ab') fragments: autologous red cell agglutination assay for HIV-1 antibodies," J Immunol Methods, 1994, 175:267-273.
Yarmush et al., "Coupling of antibody-binding fragments to solid-phase supports: site-directed binding of F(ab')2 fragments," J Biochem Biophys Methods, 1992, 25:285-297.
UniProtKB—P01034 (Cytc_HUMAN), "Cystatin-C," Jul. 21, 1986, 17 pp.
UniProtKB—P07148 (FABPL_HUMAN), "Fatty acid-binding protein, liver," Apr. 1, 1988, 16 pp.
UniProtKB—P09211 (GSTP1_HUMAN), "Gluthathione S-transferace P," Jul. 1, 1989, 22 pp.
UniProtKB—Q16035 (TIMP2_HUMAN), "Metalloproteinase inhibitor 2," Apr. 1, 1990, 18 pp.
UniProtKB—P80188 (NGAL_HUMAN), "Neutrophil gelatinase-associated lipocalin," Apr. 1, 1993, 18 pp.
UniProtKB—Q14116 (IL18_HUMAN), "Interleukin-18," Jul. 15, 1998, 21 pp.
UniProtKB—Q16270 (IBP7_HUMAN), "Insulin-like growth factor-binding protein 7," Sep. 19, 2002, 16 pp.
UniProtKB—Q16627 (CLL14_HUMAN), "Insulin-like growth factor-binding protein 7," Nov. 1, 1997, 14 pp.
UniProtKB—Q96D42 (HAVR1_HUMAN), "Hepatitis A virus cellular receptor 1," Aug. 30, 2005, 15 pp.
Official Action issued Jun. 10, 2020, in Chinese application (No. 201880012782.7).
Official Action issued Mar. 5, 2021, in Chinese application (No. 201880012782.7).
Official Action issued Aug. 4, 2021, in Chinese application (No. 201880012782.7).
Official Action issued Sep. 27, 2021, in European application (No. 18738815.2).
Official Action issued Dec. 21, 2021, in Japanese application (No. 2019-537845).
Extended European Search Report issued Nov. 13, 2020, in European application (No. 18738815.2).
Search Report issued Jun. 4, 2020, in Chinese application (No. 201880012782.7).
International Search Report issued in PCT/US2018/013561 dated Apr. 26, 2018.
Written Opinion issued in PCT/US2018/013561 dated Apr. 26, 2018.
Official Action issued Aug. 31, 2023, in Australian patent application (No. 2018207151).
Official Action issued Jan. 30, 2024, in Australian patent application (No. 2018207151).
Official Action issued Mar. 1, 2024, in Canadian patent application (No. 3049444).
Official Action issued Feb. 21, 2024, in Chinese patent application (No. 202111365747.3).
Official Action issued Nov. 28, 2023, in Mexican patent application (No. MX/a/2019/008260).

\* cited by examiner

METHODS AND COMPOSITIONS FOR EVALUATION AND TREATMENT OF RENAL INJURY AND RENAL FAILURE BASED ON C-C MOTIF CHEMOKINE LIGAND 14 MEASUREMENT

The present application claims the benefit of U.S. Provisional Patent Application 62/445,692 filed Jan. 12, 2017, which is hereby incorporated by reference in its entirety including all tables, figures and claims.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill. New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GER from reduced glomerular transcapillary pres sure, especially in patients with bilateral renal artery stenosis) | ACE inhibitors or angiotensin 11 receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnct, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis,polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerlonephritis |
| Acute tubuloin ters tidal nephritis | Drug reaction (eg, 3-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitati on | Urie acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital detects: Extrinsic: Malignancy, retroperitoneal fibrosis, ureteral trauma during surgery or high impact in jury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, *J Am Soc Nephrol* 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production<0.5 ml/kg/hr for 12 h;

"Failure": serum creatinine increased 3.0 fold from baseline OR creatinine>355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients (AKIN), which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine≥354 μmol/L accompanied by an acute increase of at least 44 μmol/L OR urine output less than 0.3 mL/kg per hour for 24 hours or anuria for 12 hours.

Likewise, Kidney Disease: Improving Global Outcomes (KDIGO) Acute Kidney Injury Work Group. KDIGO Clinical Practice Guideline for Acute Kidney Injury, Kidney inter., Suppl. 2012; 2: 1-138, refers to both RIFLE and AKIN, and offers the following AKI staging guidelines:

| Stage | Serum creatinine | or | Urine output |
|---|---|---|---|
| 1 | 1.5-1.9 times baseline<br>or<br>≥0.3 mg/di (≥26.5 mmol/l) increase | | <0.5 ml/kg/h for 6-12 hours |
| 2 | 2.0-2.9 times baseline | | <0.5 ml/kg/h for ≥12 hours |
| 3 | 3.0 times baseline<br>Or<br>Increase in serum creatinine to ≥4.0 mg/dl (≥353.6 mmol/l)<br>or<br>Initiation of renal replacement therapy | | <0.3 ml/kg/h for ≥24 hours<br>or<br>Anuria for ≥12 hours |

-continued

| Stage | Serum creatinine | or | Urine output |
|---|---|---|---|
| | or in patients <18 years, decrease in eGFR to <35 ml/min per 1.73 m2 | | |

The CIN Consensus Working Panel (McCollough et al. Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited. Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one C-C motif chemokine 14 (collectively referred to herein as "a kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

In various embodiments C-C motif chemokine 14 is used, individually or in panels comprising a plurality of kidney injury markers, for evaluating renal status in a subject. These methods comprise performing an assay method that is configured to detect C-C motif chemokine 14 in a body fluid sample obtained from the subject. The assay result, for example a measured concentration of C-C motif chemokine 14, is correlated to a likelihood of persistent AKI in a subject that is suffering from current AKI. "Current AKI" as used herein refers to characteristics classifying the subject as being at RIFLE I or F. and preferably RIFLE F, or KDIGO stage II or III, and preferably stage III.

Such a subject may be selected the subject for evaluation based on a measured value of one or more AKI biomarkers which indicate an increased risk of having an acute kidney injury that meets the definition RIFLE I or F or KDIGO Stage 2 or 3. Such biomarkers include, but are not limited to, Insulin-like growth factor-binding protein 7, Metalloproteinase inhibitor 2, Neutrophil gelatinase-associated lipocalin, Neutrophil gelatinase-associated lipocalin, Cystatin-C, Interleukin-18, Hepatitis A virus cellular receptor 1, Glutathione S-transferase P, Fatty acid-binding protein, liver, Creatinine, or combinations thereof.

In certain embodiments, the level of C-C motif chemokine 14 is used as a "rule out" for persistent AKI. In these embodiments, the measured level of C-C motif chemokine 14 can be compared to a threshold selected from a population study to separate the population into a first subpopulation below the threshold that is at a reduced likelihood of persistent AKI relative to a second subpopulation above the threshold. Such a threshold can, for example, provide a negative predictive value in the first subpopulation of at least 0.6, more preferably at least 0.7, still more preferably at least 0.75, yet more preferably at least 0.8, and most preferably at least 0.9.

In certain embodiments, the level of C-C motif chemokine 14 is used as a "rule in" for persistent AKI. In these embodiments, the measured level of C-C motif chemokine 14 can be compared to a threshold selected from a population study to separate the population into a first subpopulation above the threshold that is at an increased likelihood of persistent AKI relative to a second subpopulation below the threshold. Such a threshold can, for example, provide a positive predictive value in the first subpopulation of at least 0.6, more preferably at least 0.7, still more preferably at least 0.75, yet more preferably at least 0.8, and most preferably at least 0.9.

In certain embodiments, a subject that is "ruled out" is assigned to a treatment path for the subject's existing AKI that is "conservative," meaning it does not include renal replacement therapy (RRT). Likewise, in certain embodiments, a subject that is "ruled in" is assigned to a treatment path for the subject's existing AKI that comprises administering renal replacement therapy.

In preferred embodiments, the subject is selected for evaluation based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

Future persistence" as used herein refers to an existing acute renal injury that will continue for a period selected from the group consisting of 21 days, 14 days, 7 days, 5 days, 96 hours, 72 hours, 48 hours, 36 hours, 24 hours, and 12 hours. In certain embodiments the subject has an acute kidney injury at the time the sample is obtained. This is not meant to imply that the subject must have an acute kidney injury at the time the sample is obtained, but rather that the subject, upon onset of an acute kidney injury, suffers from an acute kidney injury that will persist A variety of methods may be used by the skilled artisan to arrive at a desired threshold value for use in these methods. For example, the threshold value may be determined from a population of subjects with non-persistent AKI by selecting a concentration representing the $75^{th}$, $85^{th}$, $90^{th}$, $95^{th}$, or $99^{th}$ percentile of C-C motif chemokine 14 measured in such normal subjects. Alternatively, the threshold value may be determined from a "diseased" population of subjects, e.g., those with persistent AKI, by selecting a concentration representing the $75^{th}$, $85^{th}$, $90^{th}$, $95^{th}$, or $99^{th}$ percentile of C-C motif chemokine 14 measured in such subjects. In another alternative, the threshold value may be determined from a prior measurement of C-C motif chemokine 14 in the same subject; that is, a temporal change in the level of C-C motif chemokine 14 in the subject may be used to assign risk to the subject.

The foregoing discussion is not meant to imply, however, that C-C motif chemokine 14 must be compared to corresponding individual thresholds. Methods for combining assay results can comprise the use of multivariate logistical regression, log linear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

As described above, in certain aspects, the measured concentration of C-C motif chemokine 14, alone or as a composite of markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1−specificity)) of greater than 1, at least about 2, more preferably at least about 3, still more preferably at least about 5, and most preferably at least about 10; or a negative likelihood ratio (calculated as (1−sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a first threshold may be used to establish a "rule-out" population, and a second threshold may be used to establish a "rule-in" population, with subjects in neither group being subjected to additional testing by the physician to establish risk.

Alternatively, thresholds may be established using "quantile analysis" in which a population is subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to have persistent AKT in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also hind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that C-C motif chemokine 14 is used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dinitrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for classifying and determination of treatment regimens in subjects suffering from acute kidney injury. In various embodiments, a measured concentration of C-C motif chemokine 14 or one or more markers related thereto, and optionally one or more additional kidney injury markers known in the art, are correlated to a likelihood of persistent AKI in the subject, and the correlation is used to guide therapy.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay arm a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quantitation). This list is not meant to be limiting.

As used herein, the term "C-C motif chemokine 14" refers to one or more polypeptides present in a biological sample that are derived from the C-C motif chemokine 14 precursor (human sequence: Swiss-Prot Q16627 (SEQ ID NO: 1)):

```
MKISVAAIPE FLLITIALGT KTESSSRGPY HPSECCFTYT TYKIPRQRIM    50

DYYETNSQCS KPGIVEITKR CHSVCTNPSD KWVODYIKDM KEN           93
```

The following domains have been identified in C-C motif chemokine 14:

| Residues | Length | Domain ID |
|---|---|---|
| 1-19 | 19 | Signal peptide |
| 20-93 | 74 | C-C motif chemokine 14 |
| 22-93 | 72 | HCC-1(3-74) |
| 23-93 | 71 | HCC-1(4-74) |
| 28-93 | 66 | HCC-1(9-74) |
| 27 | | R → QTGGKPKVVKIQLKLVG (SEQ ID NO: 2) in isoform 2 |

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay.

The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients." which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dinitrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993): Wilson (1994; J. Immunol. Methods 175:267-273; Yarmush (1992) J. Biochem. Biophys. Methods 25:85-97. The term antibody includes antigen-binding portions. i.e., "antigen binding sites." (e.g., fragments, subsequences, complementarity determining regions (CDRs)) that retain capacity to bind antigen, including (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody. (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g. Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in hulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1−specificity)) of greater than 1, at least 2, more preferably at least 3, still more preferably at least 5, and most preferably at least 10; and or a negative likelihood ratio (calculated as (1−sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61769); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase 9 (Q16790); Casein Kinase 2 (P68400); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02792; heavy chain P02794); Fructose-1,6-bisphosphatase (P09467); GRO-alpha (CXCL1, (P09341); Growth Hormone (P01241); Hepatocyte growth factor (P14210); Insulin-like growth factor I (P05019); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P05112); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (O14788); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of F1FO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (PO1160); Protein phosphatase 1-beta (PPI-beta, P62140); Rab GDI-beta (P150395); Renal kallikrein (P06870); RT1.B-1 (alpha) chain of the integral membrane protein (Q5Y7A8); soluble tumor necrosis factor receptor superfamily member 1A (sTNFR-I, P19438); soluble tumor necrosis factor receptor superfamily member 1B (sTNFR-II, P20333); Tissue inhibitor of metallopioteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatinine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, $17^{th}$ Ed., McGraw Hill, New York, pages 1741-1830, and Current Medical Diagnosis & Treatment 2008, $47^{th}$ Ed, McGraw Hill, New York, pages 785-815, each of which are hereby incorporated by reference in their entirety.

Combining assay results/clinical indicia in this manner can comprise the use of multivariate logistical regression, log linear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 $m^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60\text{mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\,corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., Nephrol. Dial. Transplant, 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, NJ, 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;
undergoing a radiographic/angiographic procedure (such as a CT scan or coronary intervention) involving the intravascular administration of contrast media;
expected to be hospitalized for at least 48 hours after contrast administration, able and willing to provide written informed consent for study participation and to comply with all study procedures.

Exclusion Criteria renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration; participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical. Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure<80 mm Hg=5 points; intra-arterial balloon pump=5 points; congestive heart failure (Class III-IV or history of pulmonary edema)=5 points; age>75 yrs=4 points; hematocrit level<39% for men, <35% for women=3 points; diabetes=3 points; contrast media volume=1 point for each 100 mL; serum creatinine level>1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2: Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, CA. The study urine samples are frozen and shipped to Astute Medical, Inc.

Example 3: Acutely Ill Subject Sample Collection

The objective of this study is to collect samples from acutely ill patients. Approximately 2200 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment;
Study population 4: approximately 1000 patients that are 21 years of age or older, within 24 hours of being admitted into the ICU, expected to have an indwelling urinary catheter for at least 48 hours after enrollment, and have at least one of the following acute conditions within 24 hours prior to enrollment:
  (i) respiratory SOFA score of ≥2 (PaO2/FiO2<300),
  (ii) (ii) cardiovascular SOFA score of ≥1 (MAP<70 mm Hg and/or any vasopressor required).
Study population 5: approximately 300 patients that are 21 years of age or older, receiving care in the ICU, have an indwelling urinary catheter as standard care at the time of enrollment, have acute kidney injury (KDIGO stage 2 or stage 3) at the time of the first sample collection, and have their first sample collected within 36 hours of meeting KDIGO stage 2 criteria
Exclusion Criteria
known pregnancy;
prisoners or institutionalized individuals;
previous renal transplantation;
comfort-measures-only status for study population 5;
known acutely worsening renal function prior to enrollment (e.g., any category of RIFLE criteria) for study populations 1, 2, 3, and 4;
received dialysis (either acute or chronic) within 5 days prior to enrollment or in imminent need of dialysis at the time of enrollment;
known infection with human immunodeficiency virus (HIV) or a hepatitis virus;
meets any of the following in study populations 4 and 5;
  (i) active bleeding with an anticipated need for >4 units PRBC in a day;
  (ii) hemoglobin<7 g/dL;
  (iii) any other condition that in the physician's opinion would contraindicate drawing serial blood samples for clinical study purposes;

meets only the SBP<90 mmHg inclusion criterion set forth above, and does not have shock in the attending physician's or principal investigator's opinion.

After obtaining informed consent, an EDTA anti-coagulated blood sample (10 mL) and a urine sample (25-50 mL) are collected from each patient. Blood and urine samples are then collected at 4 (±0.5) and 8 (±1) hours after contrast administration (if applicable); at 12 (±1), 24 (±2), 36 (±2), 48 (±2), 60 (±2), 72 (±2), and 84 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4: Immunoassay Format

Nitrocellulose membranes were pre-laminated onto backing cards and striped with test line antibody and positive control antibody. The striped nitrocellulose membranes were then cured and laminated with wicking pads and sample pads. The cards were cut into 5 mm wide test strips and placed into cartridge housings.

Purified, recombinant human C-C motif chemokine 14 protein was spiked into pooled urine and serially diluted to generate a set of standard samples covering a range of concentrations. Frozen single-use aliquots of human urine samples were thawed in a room temperature water bath for less than 20 minutes before testing.

100 µL of Test Buffer was added to a lyophilized conjugate bead containing fluorescent dye-loaded polystyrene particles coated with C-C motif chemokine 14 detect antibody. 100 µL of standard or human urine sample was added to the reconstituted conjugate solution. 100 µL of the urine sample/conjugate mixture was then loaded into the sample port of the test cartridge. At approximately 20 minutes, emitted fluorescence at 663 nm was read using a fluorescence reader upon excitation at 644 nm. A C-C motif chemokine 14 concentration was assigned to the test urine sample by comparison to a standard curve determined from the C-C motif chemokine 14 standards. Units for C-C motif chemokine 14 reported herein are ng/mL.

Example 5: Apparently Healthy Donor and Chronic Disease Patient Samples

Human urine samples from donors with no known chronic or acute disease ("Apparently Healthy Donors") were purchased from two vendors (Golden West Biologicals. Inc., 27625 Commerce Center Dr., Temecula, CA. 92590 and Virginia Medical Research. Inc., 915 First Colonial Rd., Virginia Beach, VA. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, VA. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6: Use of C-C Motif Chemokine 14 for Evaluating Renal Status in Patients Admitted to the ICU: Recovery to RIFLE 0 from RIFLE I and F Patients from the intensive care unit (ICU) with RIFLE stage of injury (I) or failure (F) are enrolled in the following study. Urine samples (50 mL) are collected from each patient at enrollment, and at every 12 hours up to day 3, and then every 24 hours thereafter up to day 7 while the subject is hospitalized. C-C motif chemokine 14 concentrations are measured in the enrollment samples by immunoassay in units of ng/mL.

Kidney status is assessed by RIFLE criteria based on serum creatinine, urine output, or both serum creatinine and urine output. Two cohorts are defined to represent a "recovered" and a "non-recovered" population. "Recovered" indicates those patients whose maximum RIFLE stage during a period of 72 hours is non-injury (RIFLE 0) where the recovery period can start from the time of sample collection to 48 hours after sample collection. "Non-recovered" indicates those patients whose maximum RIFLE stage during a period of 72 hours is risk of injury (R), injury (I) or failure (F) where the recovery period can start from the time of sample collection to 48 hours after sample collection. If a patient dies or is placed on renal replacement therapy (RRT) at any time from sample collection to 48 hours after sample collection, the patient is considered "non-recovered".

The ability to distinguish the "non-recovered" and "recovered" cohorts is quantified using the area under the receiver operating characteristic (AUC) and the following statistical measures at different concentration cutoffs: sensitivity (Sens) or true positive rate, specificity (Spec) or true negative rate, negative predictive value (NPV), positive predictive value (PPV), odds ratio (OR), and relative risk (RR). Concentration cutoffs are determined at regular percentile intervals over the range of biomarker concentrations.

TABLE 6.1

The number of non-recovered and recovered subjects, the mean (standard deviation) and median (interquartile range) concentrations for each cohort and the AUC (standard error).

| Statistic | Value |
| --- | --- |
| N (%), non-recovered | 70 (22.51%) |
| N (%), recovered | 241 (77.49%) |
| Mean (SD), non-recovered | 0.93 (1.06) |
| Mean (SD), recovered | 7.62 (21.33) |
| p, t-test | 0.009 |
| Median (IQR), non-recovered | 0.60 (0.35-1.04) |
| Median (IQR), recovered | 2.25 (0.96-6.71) |
| p. Wilcoxon rank-sum test | <0.001 |
| AUG (SE) | 0.806 (0.026) |
| p | <0.001 |

TABLE 6.2

Sensitivity, specificity, NPV, PPV, OR, and RR at cutoffs corresponding to the
$2^{nd}$ to $100^{th}$ percentile of measured C-C motif chemokine 14 concentrations.

| Pct | Cutoff | Sens (95% CI) | Spec (95% CI) | NPV (95% CI) | PPV (95% CI) | OR (95% CI) | RR (95% CI) |
|---|---|---|---|---|---|---|---|
| 2 | 0.115 | .983 (.967-1.00) | .029 (-.01-.068) | .333 (-.04-.711) | .777 (.730-.824) | 1.74 (.312-9.72) | 1.17 (.660-2.06) |
| 4 | 0.221 | .975 (.955-.995) | .086 (.020-.151) | .500 (.217-.783) | .786 (.739-.832) | 3.67 (1.15-11.8) | 1.57 (.890-2.78) |
| 6 | 0.259 | .959 (.933-.984) | .114 (.040-.189) | .444 (.215-.674) | .788 (.742-.835) | 2.98 (1.13-7.87) | 1.42 (.935-2.15) |
| 8 | 0.300 | .946 (.918-.975) | .157 (.072-.242) | .458 (.259-.658) | .794 (.748-.841) | 3.27 (1.39-7.67) | 1.47 (1.01-2.13) |
| 10 | 0.338 | .938 (.907-.968) | .229 (.130-.327) | .516 (.340-.692) | .807 (.761-.853) | 4.46 (2.08-9.59) | 1.67 (1.15-2.41) |
| 12 | 0.379 | .934 (.902-.965) | .300 (.193-.407) | .568 (.408-.727) | .821 (.776-.867) | 6.03 (2.93-12.4) | 1.90 (1.31-2.76) |
| 14 | 0.436 | .917 (.882-.952) | .329 (.219-.439) | .535 (.386-.684) | .825 (.779-.870) | 5.41 (2.75-10.6) | 1.77 (1.28-2.45) |
| 16 | 0.457 | .900 (.863-.938) | .357 (.245-.469) | .510 (.370-.650) | .828 (.783-.874) | 5.02 (2.63-9.58) | 1.69 (1.26-2.26) |
| 18 | 0.522 | .884 (.843-.924) | .400 (.285-.515) | .500 (.369-.631) | .835 (.790-.881) | 5.07 (2.73-9.42) | 1.67 (1.28-2.18) |
| 20 | 0.559 | .880 (.839-.921) | .471 (.354-.588) | .532 (.408-.656) | .851 (.807-.896) | 6.52 (3.55-12.0) | 1.82 (1.39-2.39) |
| 22 | 0.603 | .863 (.820-.906) | .500 (.383-.617) | .515 (.396-.633) | .856 (.812-.900) | 6.30 (3.48-11.4) | 1.76 (1.37-2.27) |
| 24 | 0.640 | .851 (.806-.896) | .543 (.426-.660) | .514 (.400-.627) | .865 (.821-.908) | 6.76 (3.75-12.2) | 1.78 (1.40-2.26) |
| 26 | 0.706 | .826 (.778-.874) | .557 (.441-.674) | .481 (.373-.590) | .865 (.821-.909) | 5.96 (3.35-10.6) | 1.67 (1.34-2.07) |
| 28 | 0.765 | .817 (.769-.866) | .614 (.500-.728) | .494 (.389-.599) | .879 (.837-.922) | 7.13 (3.99-12.8) | 1.74 (1.40-2.15) |
| 30 | 0.814 | .805 (.755-.855) | .657 (.546-.768) | .495 (.393-.596) | .890 (.848-.931) | 7.91 (4.40-14.2) | 1.76 (1.43-2.16) |
| 32 | 0.878 | .788 (.737-.840) | .686 (.577-.794) | .485 (.386-.583) | .898 (.855-.937) | 8.13 (4.50-14.7) | 1.74 (1.43-2.12) |
| 34 | 0.910 | .768 (.714-.821) | .714 (.608-.820) | .472 (.377-.567) | .902 (.862-.943) | 8.26 (4.54-15.0) | 1.71 (1.42-2.06) |
| 36 | 0.955 | .751 (.696-.806) | .743 (.640-.845) | .464 (.372-.557) | .910 (.870-.949) | 8.71 (4.73-16.0) | 1.70 (1.42-2.03) |
| 38 | 0.980 | .726 (.670-.782) | .743 (.640-.845) | .441 (.351-.530) | .907 (.866-.948) | 7.66 (4.18-14.0) | 1.62 (1.37-1.91) |
| 40 | 1.052 | .705 (.648-.763) | .757 (.657-.858) | .427 (.340-.514) | .909 (.868-.950) | 7.46 (4.05-13.8) | 1.59 (1.35-1.86) |
| 42 | 1.118 | .680 (.622-.739) | .771 (.673-.870) | .412 (.328-.497) | .911 (.870-.953) | 7.19 (3.87-13.4) | 1.55 (1.33-1.80) |
| 44 | 1.318 | .664 (.604-.724) | .800 (.706-.894) | .409 (.326-.491) | .920 (.879-.960) | 7.90 (4.15-15.0) | 1.56 (1.34-1.80) |
| 46 | 1.391 | .643 (.583-.704) | .814 (.723-.905) | .399 (.318-.479) | .923 (.882-.963) | 7.90 (4.09-15.3) | 1.53 (1.33-1.77) |
| 48 | 1.452 | .627 (.565-.688) | .843 (.758-.928) | .396 (.317-.474) | .932 (.893-.971) | 9.00 (4.49-18.0) | 1.54 (1.35-1.77) |
| 50 | 1.537 | .614 (.553-.676) | .886 (.811-.960) | .400 (.323-.477) | .949 (.914-.983) | 12.3 (5.65-26.9) | 1.58 (1.38-1.81) |
| 52 | 1.657 | .589 (.527-.651) | .900 (.830-.970) | .389 (.314-.464) | .953 (.919-.987) | 12.9 (5.67-29.4) | 1.56 (1.37-1.77) |
| 54 | 1.725 | .564 (.502-.627) | .900 (.830-.970) | .375 (.302-.448) | .951 (.916-.986) | 11.7 (5.13-26.5) | 1.52 (1.35-1.72) |
| 56 | 1.900 | .544 (.481-.606) | .914 (.849-.980) | .368 (.296-.439) | .956 (.922-.990) | 12.7 (5.30-30.5) | 1.51 (1.34-1.70) |
| 58 | 2.108 | .523 (.460-.586) | .929 (.868-.989) | .361 (.291-.431) | .962 (.929-.995) | 14.2 (5.54-36.6) | 1.51 (1.34-1.69) |
| 60 | 2.308 | .494 (.431-.557) | .929 (.868-.989) | .348 (.279-.416) | .960 (.925-.994) | 12.7 (4.93-32.6) | 1.47 (1.32-1.64) |
| 62 | 2.515 | .473 (.410-.536) | .943 (.888-.997) | .342 (.275-.409) | .966 (.933-.999) | 14.8 (5.23-41.9) | 1.47 (1.32-1.63) |
| 64 | 2.819 | .448 (.385-.511) | .943 (.888-.997) | .332 (.266-.397) | .964 (.930-.999) | 13.4 (4.73-37.9) | 1.44 (1.30-1.60) |
| 66 | 2.901 | .427 (.365-.490) | .957 (.910-1.00) | .327 (.263-.391) | .972 (.940-1.00) | 16.7 (5.10-54.5) | 1.44 (1.31-1.60) |
| 68 | 3.411 | .398 (.337-.460) | .957 (.910-1.00) | .316 (.253-.379) | .970 (.936-1.00) | 14.8 (4.52-48.4) | 1.42 (1.29-1.56) |
| 70 | 3.750 | .378 (.316-.439) | .971 (.932-1.01) | .312 (.250-.373) | .978 (.949-1.01) | 20.6 (4.94-86.2) | 1.42 (1.29-1.56) |
| 72 | 4.344 | .353 (.292-.413) | .971 (.932-1.01) | .304 (.243-.364) | .977 (.946-1.01) | 18.5 (4.43-77.5) | 1.40 (1.28-1.54) |
| 74 | 4.603 | .328 (.269-.387) | .971 (.932-1.01) | .296 (.237-.355) | .975 (.942-1.01) | 16.6 (3.96-69.4) | 1.38 (1.26-1.52) |
| 76 | 5.262 | .303 (.245-.361) | .986 (.958-1.01) | .291 (.233-.349) | .986 (.960-1.01) | 30.0 (4.09-220) | 1.39 (1.26-1.52) |
| 78 | 6.088 | .278 (.221-.335) | .986 (.958-1.01) | .284 (.227-.341) | .985 (.957-1.01) | 26.6 (3.62-195) | 1.38 (1.26-1.50) |
| 80 | 6.599 | .253 (.198-.308) | .986 (.958-1.01) | .277 (.222-.333) | .984 (.953-1.02) | 23.4 (3.18-172) | 1.36 (1.25-1.48) |
| 82 | 6.933 | .232 (.179-.286) | 1.00 (1.00-1.00) | .275 (.220-.329) | 1.00 (1.00-1.00) | (—) | 1.38 (1.28-1.49) |
| 84 | 8.050 | .203 (.153-.254) | 1.00 (1.00-1.00) | .267 (.214-.321) | 1.00 (1.00-1.00) | (—) | 1.36 (1.27-1.47) |
| 86 | 8.896 | .178 (.130-.227) | 1.00 (1.00-1.00) | .261 (.209-.314) | 1.00 (1.00-1.00) | (—) | 1.35 (1.26-1.45) |
| 88 | 10.847 | .154 (.108-.199) | 1.00 (1.00-1.00) | .255 (.204-.307) | 1.00 (1.00-1.00) | (—) | 1.34 (1.25-1.44) |
| 90 | 15.132 | .129 (.086-.171) | 1.00 (1.00-1.00) | .250 (.199-.301) | 1.00 (1.00-1.00) | (—) | 1.33 (1.25-1.43) |
| 92 | 18.600 | .100 (.062-.137) | 1.00 (1.00-1.00) | .244 (.194-.294) | 1.00 (1.00-1.00) | (—) | 1.32 (1.24-1.41) |
| 94 | 21.890 | .075 (.041-.108) | 1.00 (1.00-1.00) | .239 (.190-.288) | 1.00 (1.00-1.00) | (—) | 1.31 (1.23-1.40) |
| 96 | 29.526 | .050 (.022-.077) | 1.00 (1.00-1.00) | .234 (.186-.282) | 1.00 (1.00-1.00) | (—) | 1.31 (1.23-1.39) |
| 98 | 47.725 | .025 (.005-.045) | 1.00 (1.00-1.00) | .230 (.182-.277) | 1.00 (1.00-1.00) | (—) | 1.30 (1.22-1.38) |
| 100 | 293.282 | .000 (.000-.000) | 1.00 (1.00-1.00) | .225 (.179-.271) | (—) | (—) | (—) |

Example 7: Use of C-C Motif Chemokine 14 for Evaluating Renal Status in Patients Admitted to the ICU: Persistent at RIFLE F Patients from the intensive care unit (ICU) with RIFLE stage of injury (I) or failure (F) are enrolled in the following study. Urine samples (50 mL) are collected from each patient at enrollment, and at every 12 hours up to day 3, and then every 24 hours thereafter up to day 7 while the subject is hospitalized. C-C motif chemokine 14 concentrations are measured in the enrollment samples by immunoassay in units of ng/mL.

Kidney status is assessed by RIFLE criteria based on serum creatinine, urine output, or both serum creatinine and urine output. Two cohorts are defined to represent a "persistent" and a "non-persistent" population. "Persistent" indicates those patients whose minimum RIFLE stage during a period of 72 hours is failure (F) where the persistence period can start from the time of sample collection to 48 hours after sample collection. "Non-persistent" indicates those patients who are not persistent at failure (F) and whose minimum RIFLE stage during a period of 72 hours is non-injury (RIFLE 0), risk of injury (R), or injury (I) where the persistence period can start from the time of sample collection to 48 hours after sample collection. If a patient dies after failure (F) or is placed on renal replacement therapy (RRT) at any time from sample collection to 48 hours after sample collection, the patient is considered "persistent".

The ability to distinguish the "persistent" and "non-persistent" cohorts is quantified using the area under the receiver operating characteristic (AUC) and the following statistical measures at different concentration cutoffs: sensitivity (Sens) or true positive rate, specificity (Spec) or true negative rate, negative predictive value (NPV), positive predictive value (PPV), odds ratio (OR), and relative risk (RR). Concentration cutoffs are determined at regular percentile intervals over the range of biomarker concentrations.

TABLE 7.1

The number of persistent and non-persistent subjects, the mean (standard deviation) and median (interquartile range) concentrations for each cohort and the AUC (standard error).

| Statistic | Value |
|---|---|
| N (%), non-persistent | 216 (69.45%) |
| N (%), persistent | 95 (30.55%) |
| Mean (SD), non-persistent | 2.73 (6.14) |
| Mean (SD), persistent | 13.81 (31.87) |
| p, t-test | <0.001 |
| Median (IQR), non-persistent | 0.97 (0.53-2.08) |
| Median (IQR), persistent | 5.94 (2.76-15.26) |
| p, Wilcoxon rank-sum test | <0.001 |
| AUC (SE) | 0.841 (0.027) |
| p | <0.001 |

TABLE 7.2

Sensitivity, specificity, NPV, PPV, OR, and RR (95% confidence interval) at cutoffs corresponding to the $2^{nd}$ to $100^{th}$ percentile of measured C-C motif chemokine 14 concentrations.

| Pct | Cutoff | Sens (95% CI) | Spec (95% CI) | NPV (95% CI) | PPV (95% CI) | OR (95% CI) | RR (95% CI) |
|---|---|---|---|---|---|---|---|
| 2 | 0.115 | .989 (.969-1.01) | .023 (.003-.043) | .833 (.535-1.13) | .308 (.256-.360) | 2.23 (.257-19.3) | 1.85 (.307-11.2) |
| 4 | 0.221 | .989 (.969-1.01) | .051 (.022-.080) | .917 (.760-1.07) | .314 (.262-.367) | 5.04 (.642-39.6) | 3.77 (.573-24.8) |
| 6 | 0.259 | .989 (.969-1.01) | .079 (.043-.115) | .944 (.839-1.05) | .321 (.267-.374) | 8.03 (1.05-61.2) | 5.77 (.853-39.1) |
| 8 | 0.300 | .989 (.969-1.01) | .106 (.065-.148) | .958 (.878-1.04) | .328 (.273-.382) | 11.2 (1.49-84.2) | 7.86 (1.15-53.9) |
| 10 | 0.338 | .989 (.969-1.01) | .139 (.093-.185) | .968 (.906-1.03) | .336 (.280-.391) | 15.2 (2.04-113) | 10.4 (1.50 72.1) |
| 12 | 0.379 | .989 (.969-1.01) | .167 (.117-.216) | .973 (.921-1.03) | .343 (.287-.399) | 18.8 (2.54-139) | 12.7 (1.82-88.4) |
| 14 | 0.436 | .989 (.969-1.01) | .194 (.142-.247) | .977 (.932-1.02) | .351 (.294-.408) | 22.7 (3.07-167) | 15.1 (2.16-105) |
| 16 | 0.457 | .979 (.950-1.01) | .218 (.163-.273) | .959 (.904-1.01) | .355 (.297-.413) | 12.9 (3.07-54.4) | 8.70 (2.22-34.1) |
| 18 | 0.522 | .968 (.933-1.00) | .245 (.188-.303) | .946 (.887-1.01) | .361 (.302-.420) | 9.97 (3.03-32.8) | 6.73 (2.21-20.5) |
| 20 | 0.559 | .968 (.933-1.00) | .273 (.214-.333) | .952 (.898-1.01) | .369 (.310-.429) | 11.5 (3.51-37.8) | 7.64 (2.50-23.3) |
| 22 | 0.603 | .968 (.933-1.00) | .301 (.240-.362) | .956 (.907-1.00) | .379 (.318-.440) | 13.2 (4.03-43.2) | 8.58 (2.81-26.2) |
| 24 | 0.640 | .968 (.933-1.00) | .329 (.266-.391) | .959 (.915-1.00) | .388 (.326-.450) | 15.0 (4.59-49.1) | 9.58 (3.12-29.3) |
| 26 | 0.706 | .958 (.918-.998) | .356 (.293-.420) | .951 (.903-.998) | .396 (.332-.459) | 12.6 (4.46-35.6) | 8.01 (3.04-21.1) |
| 28 | 0.765 | .958 (.918-.998) | .384 (.319-.449) | .954 (.910-.998) | .406 (.342-.471) | 14.2 (5.03-40.1) | 8.84 (3.35-23.3) |
| 30 | 0.814 | .958 (.918-.998) | .412 (.346-.478) | .957 (.916-.998) | .417 (.352-.483) | 15.9 (5.65-45.0) | 9.71 (3.67-25.6) |
| 32 | 0.878 | .947 (.902-.992) | .435 (.369-.501) | .949 (.906-.993) | .425 (.358-.491) | 13.9 (5.42-35.5) | 8.41 (3.53-20.0) |
| 34 | 0.910 | .947 (.902-.992) | .468 (.401-.534) | .953 (.912-.993) | .439 (.371-.507) | 15.8 (6.18-40.4) | 9.31 (3.90-22.2) |
| 36 | 0.955 | .947 (.902-.992) | .495 (.429-.562) | .955 (.917-.994) | .452 (.383-.521) | 17.7 (6.91-45.2) | 10.1 (4.24-24.2) |
| 38 | 0.980 | .926 (.874-.979) | .514 (.447-.581) | .941 (.898-.983) | .456 (.386-.526) | 13.3 (5.88-30.0) | 7.69 (3.69-16.0) |
| 40 | 1.052 | .926 (.874-.979) | .542 (.475-.608) | .944 (.903-.984) | .471 (.399-.542) | 14.9 (6.58-33.6) | 8.34 (4.00-17.4) |
| 42 | 1.118 | .905 (.846-.964) | .565 (.499-.631) | .931 (.888-.975) | .478 (.405-.551) | 12.4 (5.93-25.9) | 6.95 (3.64-13.3) |
| 44 | 1.318 | .905 (.846-.964) | .593 (.527-.658) | .934 (.893-.976) | .494 (.420-.569) | 13.9 (6.64-29.1) | 7.52 (3.93-14.4) |
| 46 | 1.391 | .895 (.833-.956) | .616 (.551-.681) | .930 (.888-.972) | .506 (.430-.582) | 13.6 (6.69-27.7) | 7.24 (3.91-13.4) |
| 48 | 1.452 | .874 (.807-.940) | .634 (.570-.698) | .919 (.876-.963) | .512 (.435-.589) | 12.0 (6.16-23.3) | 6.36 (3.62-11.2) |
| 50 | 1.537 | .874 (.807-.940) | .662 (.599-.725) | .923 (.881-.965) | .532 (.454-.610) | 13.5 (6.95-26.4) | 6.87 (3.91-12.1) |
| 52 | 1.657 | .874 (.807-.940) | .694 (.633-.756) | .926 (.886-.966) | .557 (.477-.637) | 15.7 (8.04-30.8) | 7.52 (4.28-13.2) |
| 54 | 1.725 | .853 (.781-.924) | .713 (.653-.773) | .917 (.875-.958) | .566 (.485-.648) | 14.4 (7.58-27.2) | 6.80 (4.03-11.5) |
| 56 | 1.900 | .842 (.769-.915) | .736 (.677-.795) | .914 (.872-.955) | .584 (.501-.666) | 14.9 (7.93-27.9) | 6.77 (4.09-11.2) |
| 58 | 2.108 | .832 (.756-.907) | .759 (.702-.816) | .911 (.870-.953) | .603 (.519-.687) | 15.6 (8.37-29.0) | 6.78 (4.16-11.1) |
| 60 | 2.308 | .811 (.732-.889) | .782 (.727-.837) | .904 (.861-.946) | .621 (.536-.706) | 15.4 (8.39-28.2) | 6.45 (4.07-10.2) |
| 62 | 2.515 | .779 (.696-.862) | .796 (.743-.850) | .891 (.847-.935) | .627 (.540-.714) | 13.8 (7.66-24.8) | 5.76 (3.76-8.83) |
| 64 | 2.819 | .747 (.660-.835) | .810 (.758-.862) | .879 (.834-.925) | .634 (.545-.723) | 12.6 (7.11-22.4) | 5.26 (3.52-7.85) |
| 66 | 2.901 | .726 (.637-.816) | .829 (.778-.879) | .873 (.828-.919) | .651 (.560-.742) | 12.8 (7.24-22.8) | 5.13 (3.49-7.54) |
| 68 | 3.411 | .684 (.591-.778) | .843 (.794-.891) | .858 (.812-.905) | .657 (.563-.750) | 11.6 (6.58-20.4) | 4.64 (3.23-6.66) |
| 70 | 3.750 | .653 (.557-.748) | .856 (.810-.903) | .849 (.801-.896) | .667 (.571-.762) | 11.2 (6.35-19.8) | 4.40 (3.12-6.22) |
| 72 | 4.344 | .600 (.501-.699) | .861 (.815-.907) | .830 (.781-.880) | .655 (.555-.755) | 9.30 (5.30-16.3) | 3.86 (2.78-5.36) |
| 74 | 4.603 | .568 (.469-.668) | .875 (.831-.919) | .822 (.772-.871) | .667 (.564-.769) | 9.22 (5.20-16.3) | 3.74 (2.72-5.14) |
| 76 | 5.262 | .516 (.415-.616) | .884 (.842-.927) | .806 (.756-.856) | .662 (.554-.770) | 8.14 (4.56-14.5) | 3.41 (2.51-4.63) |
| 78 | 6.088 | .484 (.384-.585) | .898 (.858-.938) | .798 (.748-.849) | .676 (.565-.788) | 8.28 (4.56-15.0) | 3.35 (2.49-4.53) |
| 80 | 6.599 | .442 (.342-.542) | .907 (.869-.946) | .787 (.736-.838) | .677 (.561-.794) | 7.77 (4.21-14.3) | 3.18 (2.37-4.27) |
| 82 | 6.933 | .389 (.291-.488) | .912 (.874-.950) | .773 (.721-.824) | .661 (.537-.785) | 6.61 (3.54-12.4) | 2.90 (2.17-3.90) |
| 84 | 8.050 | .347 (.252-.443) | .926 (.891-.961) | .763 (.712-.815) | .673 (.542-.805) | 6.65 (3.43-12.9) | 2.85 (2.13-3.81) |
| 86 | 8.896 | .326 (.232-.421) | .944 (.914-.975) | .761 (.710-.812) | .721 (.587-.855) | 8.23 (4.00-17.0) | 3.02 (2.27-4.01) |
| 88 | 10.847 | .284 (.194-.375) | .954 (.926-.982) | .752 (.701-.803) | .730 (.587-.873) | 8.18 (3.77-17.8) | 2.94 (2.21-3.91) |
| 90 | 15.132 | .253 (.165-.340) | .968 (.944-.991) | .746 (.695-.797) | .774 (.627-.921) | 10.1 (4.17-24.4) | 3.05 (2.32-4.03) |
| 92 | 18.600 | .179 (.102-.256) | .968 (.944-.991) | .728 (.677-.780) | .708 (.526-.890) | 6.51 (2.60-16.3) | 2.61 (1.89-3.59) |
| 94 | 21.890 | .147 (.076-.219) | .981 (.964-.999) | .724 (.672-.775) | .778 (.586-.970) | 9.16 (2.93-28.7) | 2.81 (2.07-3.83) |
| 96 | 29.526 | .105 (.044-.167) | .991 (.978-1.00) | .716 (.665-.767) | .833 (.622-1.04) | 12.6 (2.70-58.7) | 2.93 (2.15-4.00) |
| 98 | 47.725 | .053 (.008-.098) | .995 (.986-1.00) | .705 (.654-.756) | .833 (.535-1.13) | 11.9 (1.38-104) | 2.82 (1.90-4.20) |
| 100 | 293.282 | .000 (.000-.000) | 1.00 (1.00-1.00) | .695 (.643-.746) | (—) | (—) | (—) |

Example 8: Use of C-C Motif Chemokine 14 with Serum Creatinine to Rule Out Persistent Renal Failure Patient cohorts, sample collections, and C-C motif chemokine 14 measurements are as described in Example 7. Serum creatinine is measured in the hospital per standard care of TCU patients, and the difference between the two serum creatinine results taken within 48 hours prior to the enrollment urine sample collection for C-C motif chemokine 14 measurement is calculated as [serum creatinine closest to enrollment]−[serum creatinine second closest to enrollment]. Patients with a difference>0 are categorized as having increasing serum creatinine and patients with a difference≤0 are categorized as having flat or decreasing serum creatinine.

Of the 99 patients with flat or decreasing serum creatinine, 82 did not develop persistent renal failure (RIFLE F) as described in Example 7, corresponding to a negative predictive value (NPV) of 83%. In the 99 patients with flat or decreasing serum creatinine, the NPV using C-C motif chemokine 14 concentration cutoffs ranging from 0.24 to 23.5 ranged from 100% to 84% (Table 8.1), higher than the NPV in all patients and higher than the NPV using the serum creatinine difference alone.

TABLE 8.1

NPV using different C-C motif chemokine 14 concentration cutoffs in all patients (N = 311) and in patients with flat or decreasing serum creatinine.

| C-C motif chemokine 14 Cutoff | NPV in All Patients | NPV in Patients with Flat or Decreasing Serum Creatinine |
|---|---|---|
| 0.24 | 93% | 100% |
| 0.34 | 97% | 100% |
| 0.44 | 96% | 100% |
| 0.56 | 95% | 100% |
| 0.69 | 96% | 100% |
| 0.82 | 96% | 100% |
| 0.93 | 95% | 98% |
| 1.06 | 94% | 96% |
| 1.38 | 93% | 95% |
| 1.55 | 92% | 95% |
| 1.83 | 91% | 93% |
| 2.31 | 90% | 93% |
| 2.88 | 88% | 91% |
| 3.75 | 85% | 89% |
| 4.95 | 81% | 89% |
| 6.60 | 79% | 90% |
| 8.63 | 76% | 89% |
| 15.24 | 75% | 87% |
| 23.50 | 72% | 84% |

Example 9: Selection of Threshold for Selecting Patients for Treatment

Based on the foregoing data, an exemplary threshold was selected at 1 ng/mL. A C-C motif chemokine 14 concentration above this threshold relates to an odds ratio for persistent AKI (RIFLE F) of 13.3, a negative predictive value of 0.94, and a positive predictive value of 0.46. If desired, other thresholds may be used. For example, a C-C motif chemokine 14 concentration a threshold of 15 ng/mL provides an odds ratio for persistent AKI of 9.3, a negative predictive value of 0.75, and a positive predictive value of 0.76. This provides an improved "rule in" of persistent AKI relative to a 1 ng/mL, but with a lower "rule out" performance.

Example 10: Use of C-C Motif Chemokine 14 in Patients Admitted to the ICU Enriched for AKI: Persistence at KDIGO Stage 3

Patients from the intensive care unit (ICU) are enrolled in the following study. EDTA anti-coagulated blood samples (10 mL), serum samples without anticoagulant (3 mL), and urine samples (50 mL) are collected from each patient at enrollment, and at every 12 hours up to day 4, and then every 24 hours thereafter up to day 7 while the subject is hospitalized.

An AKI biomarker is used to provide a subpopulation which is enriched for KDIGO stage 2 or 3 patients but which also includes KDIGO stage 1 or no KDIGO stage patients. The enriched subpopulation has at least 1.5 times or 2 times the prevalence of KDIGO stage 2 or 3 as compared to the original patient population in order to demonstrate that the initial population need not be "pure" KDIGO stage 2 or 3 in order for the CCL14 test to assign risk of persistence, and to demonstrate that AKI biomarkers can be used in conjunction with CCL14.

Urinary CCL14 is measured in the sub-population enriched for KDIGO stage 2 or 3. The resulting CCL14 concentration is used to identify patients who will develop persistent KDIGO stage 3 AKI lasting at least 72 hours ("persistent") versus those who will not develop persistent KDIGO stage 3 AKI lasting at least 72 hours ("non-persistent") within said sub-population. The procedure to determine whether a sample is included in the analysis is as follows: first, the concentration of the AKI marker for a sample is compared to a threshold; if the concentration is above the threshold, then either the urine sample collected at the same time as the AKI marker sample or the next available urine sample for which there is a valid C-C motif chemokine 14 value is used in two separate analyses. For the samples collected at the same time, the median and average time difference between the urine C-C motif chemokine 14 and plasma/serum sample collections are 0 h and 0.14 h, respectively. For the next available sample collection, the time between the AKI marker and C-C motif chemokine 14 sample collections is no more than 24 hours apart with median and average time difference of 15 h and 17 h, respectively. The concentration thresholds for the AKI markers are determined such that the proportion of KDIGO stage 2 and KDIGO stage 3 subjects above the threshold is 1.5 and 2 times the prevalence of KDIGO stage 2 and KDIGO stage 3 for the entire sample set. Kidney status of "persistent" or "non-persistent" is determined based on the time of sample collection of C-C motif chemokine 14.

Table 10.1 shows the list of AKI biomarkers, the matrix in which the biomarker is measured, the units and the two threshold concentrations (1.5× and 2×) for the coincident (0 h diff) and next available (24 h diff) C-C motif chemokine 14 sample collections.

| Swiss-Prot | Preferred Name | Abbreviation | Matrix | Units | 0 h Diff Threshold 1 (1.5×) | 0 h Diff Threshold 2 (2×) | 24 h Diff Threshold 1 (1.5×) | 24 h Diff Threshold 2 (2×) |
|---|---|---|---|---|---|---|---|---|
| Q16270 | Insulin-like growth factor-binding protein 7 | IGFBP-7 | Urine | ng/mL | 102 | 152 | 100 | 148 |
| P16035 | Metalloproteinase inhibitor 2 | TIMP-2 | Urine | ng/mL | 4.2 | 6.0 | 4.3 | 5.9 |
| Q16270 × P16035 | NephroCheck ® Test | IGFBP-7•TIMP-2 | Urine | $(ng/mL)^2$/1000 | 0.409 | 0.800 | 0.381 | 0.762 |
| P80188 | Neutrophil gelatinase-associated lipocalin | Urine NGAL | Urine | pg/mL | 49496 | 204640 | 53911 | 204640 |
| P80188 | Neutrophil gelatinase-associated lipocalin | Plasma NGAL | Blood plasma | pg/mL | 158615 | 259214 | 179702 | 275530 |
| P01034 | Cystatin-C | Plasma Cystatin C | Blood plasma | pg/mL | 2119723 | 3466083 | 2216055 | 3578438 |
| Q14116 | Interleukin-18 | Urine IL-18 | Urine | ng/mL | 0.11 | 0.31 | 0.11 | 0.29 |
| Q96D42 | Hepatitis A virus cellular receptor 1 | Urine KIM-1 | Urine | ng/mL | 6.8 | 12 | 8.3 | 13 |
| P09211 | Glutathione S-transferase P | Urine Pi-GST | Urine | ng/mL | 65 | 124 | 61 | 104 |
| P07148 | Fatty acid-binding protein, liver | Urine L-FABP | Urine | ng/mL | 34 | 115 | 32 | 232 |
| NA | Creatinine | Serum Creatinine | Blood serum | mg/dL | 0.82 | 1.0 | 0.80 | 1.1 |

Note:
IGFBP-7•TIMP-2 denotes the arithmetic product of the concentration of IGFBP-7 and TIMP-2

Kidney status is assessed by KDIGO criteria based on both serum creatinine and urine output. Two cohorts are defined to represent a "persistent" and a "non-persistent" population. "Persistent" indicates those patients whose minimum KDGO stage during a period of 72 hours is Stage 3 where the persistence period can start from the time of sample collection to 48 hours after sample collection. "Non-persistent" indicates those patients who are not persistent at KDIGO Stage 3 and whose minimum KDIGO stage during a period of 72 hours is non-AKI, KDIGO Stage 1, or KDIGO Stage 2 where the persistence period can start from the time of sample collection to 48 hours after sample collection. If a patient dies after KDIGO Stage 3 or is placed on renal replacement therapy (RRT) at any time from sample collection to 48 hours after sample collection, the patient is considered "persistent".

The ability to distinguish the "persistent" and "non-persistent" cohorts is quantified by the concentrations of C-C motif chemokine 14 in urine using the following statistical measures: area under the receiver operating characteristic (AUC), sensitivity (Sens) or true positive rate, and specificity (Spec) or true negative rate. Sensitivities and specificities are, calculated at three concentration cutoffs: the $25^{th}$ (quartile 2), $50^{th}$ (quartile 3) and $75^{th}$ (quartile 4) percentiles of C-C motif chemokine 14 concentrations.

TABLE 10.2

The area under the ROC curve (AUC) using the coincident C-C motif chemokine 14 sample collections with the different AKI markers and thresholds (1.5× and 2×), the number of samples in each analysis, the percentage of "persistent" samples and the p-value for the AUC.

| AKI Marker | AUC 1.5× | AUC 2× | nSamples 1.5× | nSamples 2× | % Persistent 1.5× | % Persistent 2× | p-value 1.5× | p-value 2× |
|---|---|---|---|---|---|---|---|---|
| IGFBP-7 | 0.77 | 0.72 | 744 | 377 | 13% | 17% | <0.0001 | <0.0001 |
| TIMP-2 | 0.80 | 0.78 | 854 | 520 | 13% | 19% | <0.0001 | <0.0001 |
| IGFBP-7•TIMP-2 | 0.80 | 0.76 | 823 | 495 | 13% | 18% | <0.0001 | <0.0001 |
| Urine NGAL | 0.83 | 0.83 | 729 | 399 | 15% | 24% | <0.0001 | <0.0001 |
| Plasma NGAL | 0.84 | 0.82 | 428 | 247 | 13% | 20% | <0.0001 | <0.0001 |
| Plasma Cystatin C | 0.85 | 0.82 | 424 | 227 | 13% | 20% | <0.0001 | <0.0001 |
| Urine IL-18 | 0.83 | 0.82 | 586 | 223 | 15% | 19% | <0.0001 | <0.0001 |
| Urine KIM-1 | 0.75 | 0.70 | 365 | 143 | 13% | 17% | <0.0001 | 0.0047 |
| Urine Pi-GST | 0.78 | 0.89 | 212 | 54 | 11% | 17% | 0.0002 | <0.0001 |
| Urine L-FABP | 0.80 | 0.84 | 206 | 68 | 16% | 26% | <0.0001 | <0.0001 |
| Serum Creatinine | 0.81 | 0.83 | 923 | 630 | 14% | 19% | <0.0001 | <0.0001 |

TABLE 10.3

C-C motif chemokine 14 cutoffs at the $25^{th}$, $50^{th}$ and $75^{th}$ percentiles of the concentration range for the coincident sample collections. Because of the different sample sizes for C-C motif chemokine 14 with the different AKI markers (see Table 10.2 above), the percentile cutoffs are determined based on each sample set used in the AUC calculations.

| AKI Marker (Abbreviation) | Cutoffs for Quartile 2 | | Cutoffs for Quartile 3 | | Cutoffs for Quartile 4 | |
|---|---|---|---|---|---|---|
|  | 1.5× | 2× | 1.5× | 2× | 1.5× | 2× |
| IGFBP-7 | 0.44 | 0.54 | 0.73 | 1.01 | 1.72 | 2.59 |
| TIMP-2 | 0.46 | 0.56 | 0.78 | 1.03 | 1.89 | 2.97 |
| IGFBP-7•TIMP-2 | 0.45 | 0.55 | 0.73 | 0.99 | 1.78 | 2.73 |
| Urine NGAL | 0.49 | 0.69 | 0.88 | 1.35 | 2.28 | 4.29 |
| Plasma NGAL | 0.54 | 0.68 | 0.99 | 1.49 | 2.41 | 4.12 |
| Plasma Cystatin C | 0.48 | 0.59 | 0.88 | 1.32 | 2.00 | 3.50 |
| Urine IL-18 | 0.50 | 0.69 | 0.88 | 1.52 | 2.39 | 3.97 |
| Urine KIM-1 | 0.57 | 0.69 | 0.94 | 1.18 | 1.93 | 3.06 |
| Urine Pi-GST | 0.51 | 0.62 | 0.80 | 1.02 | 1.84 | 5.65 |
| Urine L-FABP | 0.56 | 1.01 | 1.06 | 2.09 | 2.93 | 11.73 |
| Serum Creatinine | 0.41 | 0.50 | 0.72 | 0.97 | 1.82 | 2.54 |

TABLE 10.4

Sensitivity at each of the C-C motif chemokine 14 cutoffs and different AKI marker thresholds (1.5× and 2×) using the coincident C-C motif chemokine 14 sample collections.

| AKI Marker (Abbreviation) | Sens (95% CI) at Quartile 2 | | Sens (95% CI) at Quartile 3 | | Sens (95% CI) at Quartile 4 | |
|---|---|---|---|---|---|---|
|  | 1.5× | 2× | 1.5× | 2× | 1.5× | 2× |
| IGFBP-7 | 0.92 (0.86-0.97) | 0.86 (0.76-0.94) | 0.80 (0.72-0.88) | 0.73 (0.61-0.84) | 0.65 (0.55-0.74) | 0.54 (0.42-0.66) |
| TIMP-2 | 0.93 (0.88-0.97) | 0.88 (0.81-0.94) | 0.81 (0.73-0.88) | 0.78 (0.70-0.86) | 0.68 (0.59-0.77) | 0.64 (0.54-0.73) |
| IGFBP-7•TIMP-2 | 0.93 (0.88-0.97) | 0.89 (0.81-0.95) | 0.83 (0.75-0.89) | 0.76 (0.67-0.85) | 0.68 (0.59-0.77) | 0.60 (0.50-0.70) |
| Urine NGAL | 0.96 (0.93-0.99) | 0.97 (0.93-1.00) | 0.86 (0.80-0.93) | 0.83 (0.75-0.90) | 0.68 (0.60-0.77) | 0.57 (0.47-0.67) |
| Plasma NGAL | 0.96 (0.90-1.00) | 0.94 (0.86-1.00) | 0.89 (0.80-0.97) | 0.82 (0.70-0.92) | 0.71 (0.57-0.82) | 0.61 (0.47-0.75) |
| Plasma Cystatin C | 0.98 (0.94-1.00) | 0.96 (0.89-1.00) | 0.89 (0.80-0.96) | 0.84 (0.73-0.94) | 0.73 (0.60-0.84) | 0.62 (0.46-0.76) |
| Urine IL-18 | 0.94 (0.89-0.99) | 0.95 (0.88-1.00) | 0.86 (0.78-0.93) | 0.86 (0.74-0.96) | 0.69 (0.59-0.78) | 0.56 (0.40-0.70) |
| Urine KIM-1 | 0.89 (0.80-0.98) | 0.84 (0.68-0.96) | 0.74 (0.61-0.86) | 0.60 (0.41-0.79) | 0.57 (0.43-0.72) | 0.60 (0.41-0.79) |
| Urine Pi-GST | 0.78 (0.59-0.95) | 0.89 (0.63-1.00) | 0.74 (0.55-0.91) | 0.89 (0.63-1.00) | 0.74 (0.55-0.91) | 0.89 (0.60-1.00) |
| Urine L-FABP | 0.91 (0.80-1.00) | 1.00 (1.00-1.00) | 0.88 (0.75-0.97) | 0.83 (0.64-1.00) | 0.58 (0.40-0.74) | 0.61 (0.37-0.83) |
| Serum Creatinine | 0.94 (0.89-0.98) | 0.95 (0.91-0.98) | 0.84 (0.78-0.90) | 0.86 (0.80-0.92) | 0.69 (0.61-0.77) | 0.68 (0.59-0.76) |

TABLE 10.5

Specificity at each of the C-C motif chemokine 14 cutoffs and different AKI marker thresholds (1.5× and 2×) using the coincident C-C motif chemokine 14 sample collections.

| AKI Marker (Abbreviation) | Spec (95% CI) at Quartile 2 | | Spec (95% CI) at Quartile 3 | | Spec (95% CI) at Quartile 4 | |
|---|---|---|---|---|---|---|
|  | 1.5× | 2× | 1.5× | 2× | 1.5× | 2× |
| IGFBP-7 | 0.28 (0.24-0.31) | 0.27 (0.23-0.32) | 0.54 (0.51-0.58) | 0.55 (0.49-0.60) | 0.81 (0.78-0.84) | 0.81 (0.76-0.85) |
| TIMP-2 | 0.28 (0.25-0.31) | 0.28 (0.24-0.33) | 0.55 (0.51-0.58) | 0.57 (0.52-0.61) | 0.82 (0.79-0.84) | 0.84 (0.81-0.88) |
| IGFBP-7•TIMP-2 | 0.28 (0.25-0.31) | 0.28 (0.24-0.32) | 0.55 (0.51-0.59) | 0.56 (0.51-0.61) | 0.82 (0.79-0.84) | 0.83 (0.79-0.86) |
| Urine NGAL | 0.29 (0.25-0.33) | 0.32 (0.27-0.37) | 0.57 (0.53-0.61) | 0.61 (0.55-0.66) | 0.83 (0.80-0.86) | 0.85 (0.81-0.89) |
| Plasma NGAL | 0.28 (0.24-0.33) | 0.30 (0.24-0.37) | 0.56 (0.51-0.61) | 0.58 (0.51-0.65) | 0.82 (0.78-0.86) | 0.84 (0.79-0.89) |
| Plasma Cystatin C | 0.29 (0.24-0.34) | 0.30 (0.24-0.37) | 0.56 (0.51-0.61) | 0.59 (0.52-0.66) | 0.82 (0.78-0.86) | 0.84 (0.79-0.89) |
| Urine IL-18 | 0.29 (0.25-0.33) | 0.30 (0.24-0.37) | 0.56 (0.52-0.61) | 0.59 (0.52-0.66) | 0.83 (0.80-0.86) | 0.82 (0.77-0.88) |

TABLE 10.5-continued

Specificity at each of the C-C motif chemokine 14 cutoffs and different AKI marker thresholds (1.5× and 2×) using the coincident C-C motif chemokine 14 sample collections.

| AKI Marker | Spec (95% CI) at Quartile 2 | | Spec (95% CI) at Quartile 3 | | Spec (95% CI) at Quartile 4 | |
|---|---|---|---|---|---|---|
| (Abbreviation) | 1.5× | 2× | 1.5× | 2× | 1.5× | 2× |
| Urine KIM-1 | 0.27 (0.23-0.32) | 0.27 (0.20-0.36) | 0.54 (0.48-0.59) | 0.53 (0.44-0.61) | 0.80 (0.75-0.84) | 0.82 (0.75-0.89) |
| Urine Pi-GST | 0.26 (0.20-0.32) | 0.29 (0.17-0.43) | 0.53 (0.46-0.60) | 0.58 (0.44-0.73) | 0.81 (0.75-0.86) | 0.89 (0.79-0.98) |
| Urine L-FABP | 0.28 (0.22-0.35) | 0.36 (0.23-0.50) | 0.57 (0.50-0.65) | 0.62 (0.49-0.76) | 0.82 (0.76-0.87) | 0.88 (0.79-0.96) |
| Serum Creatinine | 0.28 (0.25-0.31) | 0.30 (0.26-0.34) | 0.56 (0.52-0.59) | 0.58 (0.54-0.63) | 0.82 (0.79-0.85) | 0.85 (0.82-0.88) |

TABLE 10.6

The area under the ROC curve (AUC) using the next available C-C motif chemokine 14 sample collections with the different AKI markers and thresholds (1.5× and 2×), the number of samples in each analysis, the percentage of "persistent" samples and the p-value for the AUC.

| AKI Marker | AUC | | nSamples | | % Persistent | | p-value | |
|---|---|---|---|---|---|---|---|---|
| (Abbreviation) | 1.5× | 2× | 1.5× | 2× | 1.5× | 2× | 1.5× | 2× |
| IGFBP-7 | 0.80 | 0.75 | 526 | 269 | 13% | 16% | <0.0001 | <0.0001 |
| TIMP-2 | 0.83 | 0.82 | 584 | 369 | 14% | 19% | <0.0001 | <0.0001 |
| IGFBP-7•TIMP-2 | 0.82 | 0.81 | 588 | 346 | 14% | 18% | <0.0001 | <0.0001 |
| Urine NGAL | 0.84 | 0.83 | 513 | 287 | 16% | 24% | <0.0001 | <0.0001 |
| Plasma NGAL | 0.86 | 0.83 | 288 | 170 | 16% | 22% | <0.0001 | <0.0001 |
| Plasma Cystatin C | 0.87 | 0.84 | 311 | 160 | 15% | 24% | <0.0001 | <0.0001 |
| Urine IL-18 | 0.84 | 0.88 | 438 | 180 | 15% | 17% | <0.0001 | <0.0001 |
| Urine KIM-1 | 0.75 | 0.68 | 220 | 82 | 14% | 18% | <0.0001 | 0.0407 |
| Urine Pi-GST | 0.84 | 0.85 | 167 | 61 | 13% | 18% | <0.0001 | <0.0001 |
| Urine L-FABP | 0.85 | 0.81 | 159 | 26 | 18% | 35% | <0.0001 | 0.0004 |
| Serum Creatinine | 0.81 | 0.85 | 645 | 430 | 15% | 19% | <0.0001 | <0.0001 |

TABLE 10.7

C-C motif chemokine 14 cutoffs at the $25^{th}$, $50^{th}$ and $75^{th}$ percentiles of the concentration range for the next available sample collections. Because of the different sample sizes for C-C motif chemokine 14 with the different AKI markers (see Table 10.2 above), the percentile cutoffs are determined based on each sample set used in the AUC calculations.

| AKI Marker | Cutoffs for Quartile 2 | | Cutoffs for Quartile 3 | | Cutoffs for Quartile 4 | |
|---|---|---|---|---|---|---|
| (Abbreviation) | 1.5× | 2× | 1.5× | 2× | 1.5× | 2× |
| IGFBP-7 | 0.38 | 0.45 | 0.63 | 0.68 | 1.63 | 2.39 |
| TIMP-2 | 0.41 | 0.46 | 0.65 | 0.77 | 1.83 | 2.69 |
| IGFBP-7•TIMP-2 | 0.40 | 0.46 | 0.64 | 0.76 | 1.66 | 2.54 |
| Urine NGAL | 0.44 | 0.63 | 0.78 | 1.27 | 2.14 | 4.36 |
| Plasma NGAL | 0.52 | 0.59 | 1.01 | 1.40 | 2.66 | 4.24 |
| Plasma Cystatin C | 0.43 | 0.48 | 0.89 | 1.22 | 2.45 | 3.54 |
| Urine IL-18 | 0.43 | 0.57 | 0.74 | 1.22 | 2.14 | 3.44 |
| Urine KIM-1 | 0.41 | 0.43 | 0.68 | 0.94 | 1.90 | 2.17 |
| Urine Pi-GST | 0.47 | 0.53 | 0.74 | 1.08 | 2.44 | 6.43 |
| Urine L-FABP | 0.52 | 0.93 | 1.07 | 1.75 | 2.98 | 11.65 |
| Serum Creatinine | 0.41 | 0.49 | 0.71 | 0.94 | 1.82 | 2.62 |

TABLE 10.8

Sensitivity at each of the C-C motif chemokine 14 cutoffs and different AKI marker thresholds (1.5× and 2×) using the next available C-C motif chemokine 14 sample collections.

| AKI Marker | Quartile 2 | | Quartile 3 | | Quartile 4 | |
|---|---|---|---|---|---|---|
| (Abbreviation) | 1.5× | 2× | 1.5× | 2× | 1.5× | 2× |
| IGFBP-7 | 0.94 (0.88-0.99) | 0.88 (0.78-0.97) | 0.84 (0.74-0.92) | 0.79 (0.67-0.90) | 0.68 (0.56-0.79) | 0.60 (0.45-0.74) |

TABLE 10.8-continued

Sensitivity at each of the C-C motif chemokine 14 cutoffs and different AKI marker thresholds (1.5× and 2×) using the next available C-C motif chemokine 14 sample collections.

| AKI Marker | Quartile 2 | | Quartile 3 | | Quartile 4 | |
|---|---|---|---|---|---|---|
| (Abbreviation) | 1.5× | 2× | 1.5× | 2× | 1.5× | 2× |
| TIMP-2 | 0.97 (0.94-1.00) | 0.91 (0.84-0.97) | 0.86 (0.78-0.93) | 0.83 (0.73-0.91) | 0.73 (0.63-0.83) | 0.70 (0.58-0.80) |
| IGFBP-7•TIMP-2 | 0.96 (0.92-1.00) | 0.90 (0.82-0.97) | 0.84 (0.75-0.92) | 0.82 (0.71-0.91) | 0.70 (0.60-0.80) | 0.69 (0.56-0.80) |
| Urine NGAL | 0.95 (0.90-0.99) | 0.96 (0.90-1.00) | 0.88 (0.80-0.94) | 0.84 (0.75-0.92) | 0.67 (0.56-0.77) | 0.59 (0.47-0.70) |
| Plasma NGAL | 0.98 (0.90-1.00) | 0.95 (0.86-1.00) | 0.91 (0.82-0.98) | 0.82 (0.68-0.93) | 0.73 (0.60-0.86) | 0.63 (0.47-0.78) |
| Plasma Cystatin C | 0.98 (0.93-1.00) | 0.97 (0.91-1.00) | 0.93 (0.85-1.00) | 0.82 (0.68-0.93) | 0.74 (0.60-0.86) | 0.66 (0.49-0.80) |
| Urine IL-18 | 0.98 (0.93-1.00) | 1.00 (1.00-1.00) | 0.88 (0.79-0.95) | 1.00 (1.00-1.00) | 0.68 (0.57-0.79) | 0.71 (0.54-0.86) |
| Urine KIM-1 | 0.97 (0.89-1.00) | 0.87 (0.67-1.00) | 0.73 (0.56-0.89) | 0.60 (0.30-0.83) | 0.60 (0.42-0.77) | 0.53 (0.27-0.80) |
| Urine Pi-GST | 0.95 (0.81-1.00) | 0.91 (0.70-1.00) | 0.82 (0.64-0.96) | 0.82 (0.55-1.00) | 0.68 (0.48-0.87) | 0.82 (0.55-1.00) |
| Urine L-FABP | 0.97 (0.88-1.00) | 1.00 (1.00-1.00) | 0.86 (0.73-0.97) | 0.78 (0.50-1.00) | 0.69 (0.51-0.85) | 0.44 (0.11-0.78) |
| Serum Creatinine | 0.94 (0.88-0.98) | 0.98 (0.94-1.00) | 0.85 (0.78-0.92) | 0.89 (0.81-0.95) | 0.67 (0.58-0.77) | 0.67 (0.56-0.77) |

TABLE 10.9

Specificity at each of the C-C motif chemokine 14 cutoffs and different AKI marker thresholds (1.5× and 2×) using the next available C-C motif chemokine 14 sample collections.

| AKI Marker | Spec (95% CI) at Quartile 2 | | Spec (95% CI) at Quartile 3 | | Spec (95% CI) at Quartile 4 | |
|---|---|---|---|---|---|---|
| (Abbreviation) | 1.5× | 2× | 1.5× | 2× | 1.5× | 2× |
| IGFBP-7 | 0.28 (0.24-0.32) | 0.28 (0.22-0.34) | 0.55 (0.51-0.60) | 0.56 (0.49-0.62) | 0.81 (0.78-0.85) | 0.82 (0.77-0.87) |
| TIMP-2 | 0.29 (0.25-0.33) | 0.29 (0.24-0.34) | 0.56 (0.51-0.60) | 0.58 (0.52-0.63) | 0.83 (0.79-0.86) | 0.85 (0.81-0.89) |
| IGFBP-7•TIMP-2 | 0.29 (0.25-0.33) | 0.28 (0.24-0.34) | 0.55 (0.51-0.60) | 0.57 (0.51-0.63) | 0.82 (0.79-0.86) | 0.85 (0.80-0.89) |
| Urine NGAL | 0.29 (0.25-0.33) | 0.32 (0.26-0.38) | 0.57 (0.52-0.62) | 0.61 (0.54-0.67) | 0.83 (0.79-0.86) | 0.85 (0.81-0.90) |
| Plasma NGAL | 0.30 (0.24-0.35) | 0.31 (0.24-0.40) | 0.58 (0.51-0.64) | 0.59 (0.51-0.68) | 0.84 (0.79-0.89) | 0.86 (0.81-0.92) |
| Plasma Cystatin C | 0.29 (0.24-0.35) | 0.33 (0.25-0.41) | 0.58 (0.52-0.64) | 0.60 (0.52-0.69) | 0.83 (0.79-0.88) | 0.88 (0.82-0.93) |
| Urine IL-18 | 0.29 (0.25-0.34) | 0.31 (0.24-0.39) | 0.57 (0.52-0.62) | 0.60 (0.53-0.68) | 0.83 (0.79-0.87) | 0.85 (0.79-0.90) |
| Urine KIM-1 | 0.29 (0.23-0.36) | 0.28 (0.18-0.39) | 0.54 (0.47-0.61) | 0.52 (0.41-0.65) | 0.81 (0.75-0.86) | 0.82 (0.72-0.91) |
| Urine Pi-GST | 0.28 (0.21-0.36) | 0.30 (0.19-0.45) | 0.55 (0.47-0.63) | 0.58 (0.45-0.73) | 0.81 (0.75-0.88) | 0.88 (0.79-0.96) |
| Urine L-FABP | 0.30 (0.23-0.38) | 0.41 (0.20-0.67) | 0.58 (0.50-0.67) | 0.65 (0.44-0.89) | 0.85 (0.79-0.91) | 0.88 (0.71-1.00) |
| Serum Creatinine | 0.28 (0.25-0.32) | 0.30 (0.26-0.35) | 0.56 (0.52-0.60) | 0.59 (0.54-0.64) | 0.82 (0.79-0.86) | 0.85 (0.81-0.89) |

Example 11: Use of C-C Motif Chemokine 14 in Managing Patient Care

A 65 year-old male is admitted to the intensive care unit (ICU) after presenting to the emergency department with a diagnosis of a severe, community acquired pneumonia. Due to worsening respiratory insufficiency and an inability to maintain adequate oxygenation, he is intubated and placed on mechanical ventilation. He also is noted to have a low blood pressure and received several liters of intravenous (IV) crystalloid intravenous fluid for volume resuscitation. He does not respond and, as a result, vasopressor therapy is started to maintain systemic blood pressure. He is also pancultured and placed on broad-spectrum antimicrobial therapy.

His urine output is persistently below than 0.3 mL/kg/hr since his admission despite the aggressive volume resuscitation that he received and his serum creatinine rises from his admission level of 1.3 mg/dL to 5.1 mg/dL, suggesting KDIGO stage III (RIFLE F). He requires significant positive pressure ventilatory support, including elevated FiO2 and PEEP. His C-C motif chemokine 14 level is drawn at this time in view of severe AKI.

A C-C motif chemokine 14 concentration at this time of less than 1 ng/mL indicates an increases likelihood recovery from AKI and a likely return of renal function. Such a patient can be safely managed with conservative therapy, which includes diuretic therapy, predominantly with loop diuretics, usually provided intravenously either intermittently or via continuous intravenous infusion. While diuretic therapy will need to be closely monitored, both in general and especially in patients with AKI, in view of the effect upon electrolyte levels and volume shifts, conservative management with diuretics is nevertheless beneficial as it can help avoid sudden fluid shifts and electrolyte fluxes seen with more aggressive interventions, a phenomenon that is likely heightened in AKI due to a reduced physiologic reserve as a result of the presence multiple comorbidities and concomitant organ system failures.

Diuretic therapy requires the close evaluation of common electrolytes, especially sodium, potassium, chloride, but also magnesium, calcium, and phosphorus, not only to aid in the assessment of AKI improvement but also as a result of electrolyte losses and alterations in hydrogen ions and bicarbonate losses that occur secondary to diuretic agents and diuresis.

Conversely, a C-C motif chemokine 14 concentration at this time of 15 ng/mL indicates an increased likelihood of persistent AKI. The physician initiates renal replacement therapy, and electrolyte and physiologic monitoring. While awaiting RRT and insertion of the dialysis catheter, the patient is given standard medical treatment to attenuate hyperkalemia including agents to stabilize cardiac membranes and reduce membrane irritability (e.g. intravenous calcium), and agents to facilitate the intracellular shift of potassium into the cells (e.g. sodium bicarbonate, insulin and concurrent glucose administration, inhaled beta adrenergic agents such as albuterol). Potassium is removed from all intravenous solutions.

Example 12: Use of C-C Motif Chemokine 14 in Managing Patient Care

A 59 year old female with a history of insulin dependent diabetes mellitus, hypertension, and chronic obstructive pulmonary disease (COPD), the latter of which has required systemic steroid therapy, is admitted to the intensive care unit (ICU) with a diagnosis of sepsis presumed secondary to a urinary tract infection. The patient is febrile with a temperature of 102.3° F. and also exhibits an elevated white count with a significant bandemia and a high anion gap metabolic acidosis with an elevated serum lactate. She is noted to be profoundly hypotensive upon admission to the hospital (MAP<60 mm Hg) and after initial resuscitation in the emergency department which included intravenous admission of several liters of crystalloid therapy in addition to colloid solution, the patient is placed upon continuous infusion of intravenous vasopressor therapy, including norepinephrine and vasopressin, to maintain her mean arterial pressure (MAP) and improve perfusion of her vital organs. She is also intubated and placed on mechanical ventilation in view of impending respiratory failure. A triple lumen central venous catheter is also placed in the right internal jugular vein to facilitate infusion of the vasoactive agents and also monitor her central venous pressure. A left radial arterial catheter is also placed to enable continuous assessment of her systemic blood pressure and facilitate frequent blood sampling. Blood and urine cultures are drawn within forty minutes of presentation to the hospital and broad spectrum antimicrobial therapy is also initiated to treat the patient for the most likely infectious pathogens.

The patient has a baseline serum creatinine of 1.5 mg/dL, and her initial creatinine upon presentation to the hospital is measured at 2.3 mg/dL, which rises to 3.4 after 24 hours. Her urine output is minimal, despite the aggressive volume resuscitation and initiation of vasopressor therapy, and never exceeds 0.3 ml/kg/hr, suggesting a severe AKI (AKI Stage III by KDIGO criteria, RIFLE F). After 48 hours in the ICU, she remains intubated, although her oxygenation improves and her FiO2 is reduced to 45%, with a PEEP of 5. Her acidosis also improves slightly, although she still requires vasopressor therapy to maintain her mean arterial pressure (MAP) above 65 mm Hg. In view of her elevated serum creatinine, her persistently low urine output, and hence her diagnosis of AKI stage III, a C-C motif chemokine 14 concentration is drawn at this time.

A C-C motif chemokine 14 concentration at this time of less than 1 ng/mL indicates an increased likelihood recovery from AKI and a likely return of renal function. There is an added benefit of treating exclusively with conservative management (and hence not employing or initiating RRT) in view of reducing the likelihood of significant volume and electrolyte shifts that frequently occur with AKI, especially in unstable patients like this with systemic illness, multiorgan failure, and hemodynamic insufficiency.

Conversely, a C-C motif chemokine 14 concentration at this time of 15 ng/mL indicates an increased likelihood of persistent AKI. The physician initiates renal replacement therapy, and closely monitors electrolyte and physiologic parameters. While awaiting RRT and insertion of the dialysis catheter, the patient is given standard medical treatment to attenuate hyperkalemia including agents that stabilize cardiac membranes and reduce membrane irritability (e.g. intravenous calcium), and agents to facilitate the intracellular shift of potassium into the cells (e.g. sodium bicarbonate, insulin and concurrent glucose administration, inhaled beta adrenergic agents such as albuterol). Potassium is removed from all intravenous solutions.

Example 13: Use of C-C Motif Chemokine 14 in Managing Patient Care

A 71 year-old female with a history of mild congestive heart failure, hyperlipidemia, and hypertension, is admitted to the hospital with progressive shortness of breath upon exertion along with worsening pedal edema and reduced exercise tolerance, with increased breathlessness upon mild exertion and performance of her household chores. She is followed by her private physician for many years and a recent echocardiogram demonstrates left ventricular hypertension and hypertrophy, a reduced ejection fraction, and mild aortic insufficiency. Upon admission to the hospital, the patient has a slightly reduced systolic blood pressure and is noted to have mild jugular venous distension, an S3, bibasilar rales, and 2+ pitting edema on physical examination, along with a chest xray suggestive of pulmonary vascular congestion consistent with CHF. Her ECG does not show evidence of an ACS/MI although she does have a left axis deviation and LVH. Her serum creatinine has risen to 2.7 mg/DL from her baseline of 0.8 and her urine output is noted to be consistently low during the first 36 of her admission, below 0.5 ml/kg/hr. Her dyspnea slightly improves with medical treatment although her urine output does not increase with both medical therapy and cautious intravenous hydration.

The patient is diagnosed with severe AKI (KDIGO criteria stage II-III) and of note, her potassium continues to rise to a level of 6.1 mEq/L. There are no ECG changes or conduction defects (both 12 lead and continuous ECG monitor) consistent with hyperkalemia although the patient does have occasional ventricular ectopy (PVC's, singlets, non-sustained). She does not have a significant acidosis and is also not on any medications that have been associated with elevated serum potassium levels (e.g. potassium sparing diuretics). Her C-C motif chemokine 14 level is drawn at this time in view of severe AKI.

A C-C motif chemokine 14 concentration at this time of less than 1 ng/mL indicates an increases likelihood recovery from AKI and a likely return of renal function. The patient's hyperkalemia is managed with conservative therapy with medical therapies and to reduce her serum potassium along with appropriate electrolyte and physiologic monitoring. These therapies include agents to stabilize cardiac membranes and reduce the membrane irritability (e.g. intravenous calcium), agents to facilitate the intracellular shift of potassium into the cells (e.g. sodium bicarbonate, insulin and concurrent glucose administration, inhaled beta adrenergic agents such as albuterol), and agents to remove excess potassium (e.g. potassium binding resins such as sodium polystyrene sulfonate—either alone or with sorbitol). An order is entered to ensure that all potassium is removed from all intravenous solutions and a low potassium diet is also initiated. Serum potassium, in concert with other electrolytes, acid-base status are also monitored several times a day during the treatment for elevated potassium and the patient is also continued on her continuous ECG monitor to assess for any potassium related electromechanical changes.

Conversely, a C-C motif chemokine 14 concentration at this time of 15 ng/mL indicates an increased likelihood of persistent AKI. The physician initiates renal replacement therapy, and electrolyte and physiologic monitoring. While awaiting RRT and insertion of the dialysis catheter, the patient is given standard medical treatment to attenuate hyperkalemia including agents to stabilize cardiac membranes and reduce membrane irritability (e.g. intravenous calcium), and agents to facilitate the intracellular shift of potassium into the cells (e.g. sodium bicarbonate, insulin and concurrent glucose administration, inhaled beta adrenergic agents such as albuterol). Potassium is removed from all intravenous solutions and a low potassium diet is also initiated.

Example 14: Use of C-C Motif Chemokine 14 in Managing Patient Care

A 67 year-old male with a history of congestive heart failure (New York Heart Association Class II-III), on multiple medications including ACE inhibitors and ARBs, also with a history of hyperlipidemia, hypertension, diabetes (adult onset) and peripheral vascular disease, is admitted to the hospital with worsening shortness of breath especially upon exertion and worsening pedal and peripheral edema. He is being followed by both his private physician and cardiologist and his most recent echocardiogram shows a reduced ejection fraction, worsening aortic and mitral insufficiency, and increased left ventricular hypertrophy. Upon admission to the hospital, his blood pressure is 155/95, his heart rate is 110 (normal sinus rhythm), and he has bibasilar rales and 2+ pitting edema, and his cardiomegaly and bilateral pulmonary vascular congestion that is worse from a chest xray performed 5 months earlier. His ECG shows occasional PVCs, a left axis deviation, and LVH. His serum creatinine has risen to 3.3 mg/DL from a baseline of 1.3 and his urine output is noted to be consistently low during the first 36 of admission, below 0.5 ml/kg/hr. which only minimal improvement following administration of intravenous diuresis. He is admitted to the TCU and a decision is made to start him on dobutamine for inotropic support. Of note, the patient is on digoxin, which is initially held due to an elevated level on admission.

The patient is diagnosed with severe AKI (KDIGO criteria stage II-III) and his serum potassium continues rose to a level of 6.3 mEq/L. He does have some peaked T-waves throughout the precordial leads on his ECG, although his QRS complex remained unchanged on 12-lead and continuous ECG monitor). His scrum pH is 7.35 His C-C motif chemokine 14 level is drawn at this time in view of severe AKI.

A C-C motif chemokine 14 concentration at this time of less than 1 ng/mL indicates an increases likelihood recovery from AKI and a likely return of renal function. Such a patient can be safely managed with conservative therapy, which includes diuretic therapy, predominantly with loop diuretics, usually provided intravenously either intermittently or via continuous intravenous infusion. While diuretic therapy will need to be closely monitored, both in general and especially in patients with AKI, in view of the effect upon electrolyte levels and volume shifts, conservative management with diuretics is nevertheless beneficial as it can help avoid sudden fluid shifts and electrolyte fluxes seen with more aggressive interventions, a phenomenon that is likely heightened in AKI due to a reduced physiologic reserve as a result of the presence multiple comorbidities and concomitant organ system failures.

Diuretic therapy requires the close evaluation of common electrolytes, especially sodium, potassium, chloride, but also magnesium, calcium, and phosphorus, not only to aid in the assessment of AKI improvement but also as a result of electrolyte losses and alterations in hydrogen ions and bicarbonate losses that occur secondary to diuretic agents and diuresis.

Conversely, a C-C motif chemokine 14 concentration at this time of 15 ng/mL indicates an increased likelihood of persistent AKI. The physician initiates renal replacement therapy, and electrolyte and physiologic monitoring. While awaiting RRT and insertion of the dialysis catheter, the patient is given standard medical treatment to attenuate hyperkalemia including agents to stabilize cardiac membranes and reduce membrane irritability (e.g. intravenous calcium), and agents to facilitate the intracellular shift of potassium into the cells (e.g. sodium bicarbonate, insulin and concurrent glucose administration, inhaled beta adrenergic agents such as albuterol). Potassium is removed from all intravenous solutions and a low potassium diet is also initiated.

Example 15: Use of C-C Motif Chemokine 14 in Managing Patient Care

A 51 year old male with no significant past medical or surgical history, presents to the emergency department with the severe of abdominal pain, associated with nausea, vomiting, fever, and chills, and worsened by sudden movement or change in position. He denies a history of tobacco, alcohol, or drug abuse and is on no medications. He is generally healthy, with no history of diabetes, hypertension, COPD, cardiac disease, peptic ulcer disease or other gastrointestinal pathology, and he has no history of bowel, bladder, renal, or hepatic issues or pathology. His wife states that he began to complain of abdominal pain about 4 days ago and did not eat or drink for the past two days. When he is unable to get out of bed and is noted to be diaphoretic and moaning in pain, she calls EMS which brings him to the emergency department.

Upon presentation to the hospital, the patient is noted to be tachypnea and tachycardic, with a heart rate of 120 (normal sinus rhythm), a blood pressure of 105/58, and a respiratory rate of 20. His chest is clear, his cardiac examination is normal (with the exception of the tachycardia), however; examination of his abdomen reveals significant guarding and rebound tenderness in all quadrants but most notably in the right lower quadrant. His temperature as 100.8° F., his white blood cell count is 19.0 with 88% immature forms, and he has a serum lactate of 2.3, an anion gap of 16, and a blood gas of 7.36/36/88 on 2 liters nasal cannula $O_2$. A chest x-ray is performed which shows no pulmonary pathology however some subdiaphragmatic air is noted on the right. An abdominal CT is performed which suggests appendicitis and a surgeon is immediately consulted. The patient is taken to the operating room for surgical intervention. The patient is noted to have a ruptured appendix and diffuse peritonitis. Otherwise his surgery is uneventful and he is transferred to the recovery room and then the ICU, still intubated. Broad-spectrum antibiotics are initiated in the emergency department and continued in view of the acute abdomen and peritonitis. Multiple blood and peritoneal cultures are sent.

The patient remains intubated and he continues to required significant and increased intravenous fluid infusion for several days (balanced crystalloid therapy are the predominant fluids that are provided) due to his tenuous blood pressure (low MAP) and minimal urine output (less than 0.3 ml/kg/hr). His blood pressure continues to fall despite aggressive fluid hydration and vasopressor therapy is also initiated. In addition, his white count continues to rise, he continues to spike temperatures, he also appears to sequester intraabdominal fluid and accumulate fluid in his third space. His ventilatory needs also worsen, as he requires increased FiO2 and PEEP, suggestive of septic ARDS. Of note, his serum creatinine—which is 0.8 mg/dL upon admission—rises to 4.4 mg/dL by day #3. His lactate initially falls following surgery but it rose to 2.6 on day 2. The patient also has a low serum bicarbonate and a worsening anion gap acidosis. His serum pH is 7.21 with a pCO2 of 26 and a pO2 of 78, on 75% FiO2, tidal volume of 500 (the patient's ideal body weight is 90 kg), a PEEP of 8, and a respiratory rate of 26 (rate is set at 20 breaths per minute).

On the basis of the patient's serum creatinine and low urine output, he is diagnosed with severe AKI (KDIGO Stage III). He also has a severe acidosis and academia as a result of several factors, including his sepsis and its associated sequelae, his persistently low MAP, and his AKI. His C-C motif chemokine 14 level is drawn at this time in view of severe AKI.

A C-C motif chemokine 14 concentration at this time of less than 1 ng/mL indicates an increases likelihood recovery from AKI and a likely return of renal function. As a result the decision is made to manage this patient's condition and his acidosis with conservative therapy. Acidosis can be aggressively managed by medical therapy and close monitoring by the following approaches:

Treatment of the underlying disease (e.g. treatment of infection, sepsis, cardiac insufficiency, severe arrhythmias, respiratory failure, etc)

Correction of volume deficits and intravascular volume depletion, as described in prior sections.

Use of vasopressor and vasoactive agents, as described in prior sections.

Blood and blood product transfusions, when severe anemia is present

Treatment of severe hypothermia, if present

Hyperventilation and adjustment of ventilatory parameters in patients who require mechanical ventilation.

Sodium Bicarbonate (NaHCO3) may also be beneficial when acidosis is severe.

Patients with severe acidosis will also require close evaluation of their electrolytes, especially their serum potassium, in view of the intracellular and extracellular shifts that ensue, and serum sodium, especially when the patients receive sodium bicarbonate, antimicrobial therapies which contain sodium solutions and electrolyte, and other sodium and salt based solutions.

Conversely, a C-C motif chemokine 14 concentration at this time of 15 ng/mL indicates an increased likelihood of persistent AKI. The physician initiates renal replacement therapy, and electrolyte and physiologic monitoring. While awaiting RRT and insertion of the dialysis catheter, the patient is given standard medical treatment to attenuate hyperkalemia including agents to stabilize cardiac membranes and reduce membrane irritability (e.g. intravenous calcium), and agents to facilitate the intracellular shift of potassium into the cells (e.g. sodium bicarbonate, insulin and concurrent glucose administration, inhaled beta adrenergic agents such as albuterol). Potassium is removed from all intravenous solutions.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating renal status in a subject that is diagnosed as having an acute kidney injury (AKI), wherein the subject meets the definition RIFLE I or F or KDIGO Stage 2 or 3, and treating the subject based on the evaluation, the method comprising:
   (a) performing an assay configured to detect C-C motif chemokine 14 on a body fluid sample obtained from the subject to provide an assay result indicating a level of C-C motif chemokine 14 in the sample;
   (b) determining that the subject is likely to respond favorably to diuretic treatment when the level of C-C motif chemokine 14 in the sample is below a predetermined threshold; and
   (c) treating the subject having the level of C-C motif chemokine 14 below the predetermined threshold with diuretic therapy.

2. The method of claim 1, wherein the body fluid is urine, blood, serum, or plasma.

3. The method of claim 2, wherein said assay result is a measured urine concentration of C-C motif chemokine 14.

4. The method of claim 1, wherein the subject is diagnosed as having an acute kidney injury meeting the definition RIFLE F or KDIGO Stage 3 at the time the time the body fluid sample is obtained.

5. A method for evaluating renal status in a subject and treating the subject based on the evaluation, comprising:
   (a) selecting the subject for evaluation based on a measured value of one or more AKI biomarkers that exceeds a threshold indicative of an increased risk of having an acute kidney injury that meets the definition RIFLE I or F or KDIGO Stage 2 or 3;
   (b) performing an assay configured to detect C-C motif chemokine 14 on a body fluid sample obtained from the subject to provide an assay result indicating a level of C-C motif chemokine 14 in the sample;
   (c) determining that the subject is likely to respond favorably to diuretic treatment when the level of C-C motif chemokine 14 in the sample is below a predetermined threshold; and
   (d) treating the subject having the level of C-C motif chemokine 14 below the predetermined threshold with diuretic therapy.

6. The method of claim 5, wherein the AKI biomarkers are one or more of Insulin-like growth factor-binding protein 7, Metalloproteinase inhibitor 2, Neutrophil gelatinase-associated lipocalin, Cystatin-C, Interleukin-18, Hepatitis A virus cellular receptor 1, Glutathione S-transferase P, Creatinine, and Fatty acid-binding protein, liver, including combinations thereof.

7. The method of claim 5, wherein the body fluid is urine, blood, serum, or plasma.

8. The method of claim 7, wherein said assay result is a measured urine concentration of C-C motif chemokine 14.

9. The method of claim 5, wherein the subject is diagnosed as having an acute kidney injury meeting the definition RIFLE F or KDIGO Stage 3 at the time the time the body fluid sample is obtained.

10. The method of claim 1, wherein the assay result is a measured concentration of C-C motif chemokine 14.

11. The method of claim 1, wherein the method further comprises contacting all or a portion of the body fluid sample with a binding reagent that specifically binds to C-C motif chemokine 14.

12. The method of claim 11, wherein the binding reagent is an antibody.

13. The method of claim 1, wherein the assay is an immunoassay.

14. The method of claim 13, wherein the assay is a sandwich immunoassay.

15. The method of claim 1, wherein the assay is a competitive binding assay.

16. The method of claim 5, wherein the assay result is a measured concentration of C-C motif chemokine 14.

17. The method of claim 5, wherein the method further comprises contacting all or a portion of the body fluid sample with a binding reagent that specifically binds to C-C motif chemokine 14.

18. The method of claim 17, wherein the binding reagent is an antibody.

19. The method of claim 5, wherein the assay is an immunoassay.

20. The method of claim 19, wherein the assay is a sandwich immunoassay.

21. The method of claim 5, wherein the assay is a competitive binding assay.

* * * * *

SEQUENCE LISTING

```
<160> NUMBER OF SEQ ID NOS: 2

<210> SEQ ID NO 1
<211> LENGTH: 93
<212> TYPE: PRT
<213> ORGANISM: Homo sapiens
<220> FEATURE:
<221> NAME/KEY: misc_feature
<223> OTHER INFORMATION: C-C motif chemokine 14 precursor

<400> SEQUENCE: 1

Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
            20                  25                  30

Ser Glu Cys Cys Phe Thr Tyr Thr Thr Tyr Lys Ile Pro Arg Gln Arg
        35                  40                  45

Ile Met Asp Tyr Tyr Glu Thr Asn Ser Gln Cys Ser Lys Pro Gly Ile
    50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Gln Thr Gly Gly Lys Pro Lys Val Val Lys Ile Gln Leu Lys Leu Val
1               5                   10                  15

Gly
```